US008921525B2

(12) United States Patent
Kumagai et al.

(10) Patent No.: US 8,921,525 B2
(45) Date of Patent: Dec. 30, 2014

(54) HIGHLY-FUNCTIONAL MUTANT OF HUMANIZED ANTI-EGFR ANTIBODY VARIABLE REGION

(75) Inventors: Izumi Kumagai, Sendai (JP); Takeshi Nakanishi, Sendai (JP); Ryutaro Asano, Sendai (JP); Mitsuo Umetsu, Sendai (JP)

(73) Assignee: Tohoku University, Sendai-Shi (JP)

( * ) Notice: Subject to any disclaimer, the term of this patent is extended or adjusted under 35 U.S.C. 154(b) by 40 days.

(21) Appl. No.: 13/510,516

(22) PCT Filed: Nov. 11, 2010

(86) PCT No.: PCT/JP2010/070127
§ 371 (c)(1),
(2), (4) Date: Aug. 27, 2012

(87) PCT Pub. No.: WO2011/062112
PCT Pub. Date: May 26, 2011

(65) Prior Publication Data
US 2013/0131320 A1 May 23, 2013

(30) Foreign Application Priority Data
Nov. 18, 2009 (JP) .................................. 2009-263147

(51) Int. Cl.
*C07K 16/22* (2006.01)
*C07K 16/30* (2006.01)
*C07K 16/28* (2006.01)

(52) U.S. Cl.
CPC ........... *C07K 16/22* (2013.01); *C07K 2317/626* (2013.01); *C07K 16/2863* (2013.01); *C07K 2317/92* (2013.01); *C07K 2317/565* (2013.01); *C07K 2317/567* (2013.01); *C07K 16/2809* (2013.01); *C07K 2317/622* (2013.01); *C07K 2317/31* (2013.01); *C07K 2317/24* (2013.01); *C07K 2317/73* (2013.01)
USPC .................. 530/387.3; 530/387.7; 530/388.8; 530/388.85; 536/23.53; 435/252.33; 435/320.1; 435/69.1

(58) Field of Classification Search
CPC .............. C07K 16/22; C07K 16/2863; C07K 2317/24; C07K 2317/565; C07K 2317/626
See application file for complete search history.

(56) References Cited

U.S. PATENT DOCUMENTS

| 4,943,533 | A * | 7/1990 | Mendelsohn et al. ... 530/388.22 |
| 7,635,475 | B2 * | 12/2009 | Kumagai et al. ............ 424/136.1 |
| 2006/0210564 | A1 | 9/2006 | Kumagai et al. |
| 2009/0202532 | A1 | 8/2009 | Kumagai et al. |

FOREIGN PATENT DOCUMENTS

| EP | 2 006 379 A1 | 12/2008 |
| JP | 2004-242638 A | 9/2004 |
| JP | 2010-119303 A | 6/2010 |
| WO | WO 02/06486 A1 | 1/2002 |
| WO | WO 2007/108152 A1 | 9/2007 |
| WO | WO 2010/109924 A1 | 9/2010 |

OTHER PUBLICATIONS

Asano et al. Clin Cancer Res 2006; 12:4036-42.*
Paul, Fundamental Immunology, 3rd Edition, 1993, pp. 292-295.*
Muyldermans, Rev Mol Biotech 2001; 74:277-302.*
Rudikoff et al., Proc. Nat'l Acad. Sci. USA 1982; 79:1979-83.*
Brown et al., J. Immunol. 1996; 156(9):3285-91.*
Makabe et al., J Biol Chem 2008; 283:1156-66.*
Asano et al., "Highly Effective Recombinant Format of a Humanized IgG-like Bispecific Antibody for Cancer Immunotherapy with Retarding of Lymphocytes to Tumor Cells," The Journal of Biological Chemistry (Sep. 21, 2007), vol. 282, No. 38, pp. 27659-27665.
Extended European Search Report issued Dec. 3, 2012, in European Patent Application No. 10831507.8.
Nakanishi et al., "Development of an affinity-matured humanized anti-epidermal growth factor receptor antibody for cancer immunotherapy," Protein Engineering Design & Selection (2012), pp. 1-10.
International Search Report issued Feb. 8, 2011, in PCT International Application No. PCT/JP2010/070127, with English translation.
Kortt et al., "Dimeric and trimeric antibodies: high avidity scFvs for cancer targeting," Biomolecular Engineering (2001), vol. 18, pp. 95-108.
Lamminmaki et al., "Expanding the Conformational Diversity by Random Insertions to CDRH2 Results in Improved Anti-estradiol Antibodies," J. Mol. Biol. (1999), vol. 291, pp. 589-602.
Merienne et al., "The Functional Architecture of an Acetylcholine Receptor-mimicking Antibody," The Journal of Biological Chemistry (Sep. 19, 1997), vol. 272, No. 38, 23775-23783.
Tsumoto, K. and I. Kumagai.,"Thermodynamic and kinetic analyses of the antigen-antibody interaction using mutants," The Japanese Society for Artificial Intelligence Chishiki Base System Kenkyukai Shiryo (2000), vol. 49, pp. 83-88, with English abstract.

* cited by examiner

*Primary Examiner* — Sheela J Huff
*Assistant Examiner* — Jessica H Roark
(74) *Attorney, Agent, or Firm* — Birch, Stewart, Kolasch & Birch, LLP

(57) ABSTRACT

[Problem]
Disclosed is an antibody that exhibits excellent cytotoxicity and cell growth inhibition and that is based on an anti-human epithelial cell growth factor receptor (1) (Her1) antibody (528). Further disclosed is a method for producing same, and the like.
[Solution]
The mutant of an H chain humanized variable region (5H) or an L chain humanized variable region (5L) of the anti-human epithelial cell growth factor receptor (1) (Her1) antibody (528) is the aforementioned antibody characterized by having one to a plurality (for example: 1 to 5, or 1 to 3) of amino acid mutations within CDR2. Further disclosed are antibody molecules containing said region, a nucleic acid molecule coding for these polypeptides, a method for producing said antibody molecules, and the like.

22 Claims, 11 Drawing Sheets
(10 of 11 Drawing Sheet(s) Filed in Color)

Fig.1  Introduction of mutation based on the steric structure of a fragment of the variable region of a humanized 528

Fig.9
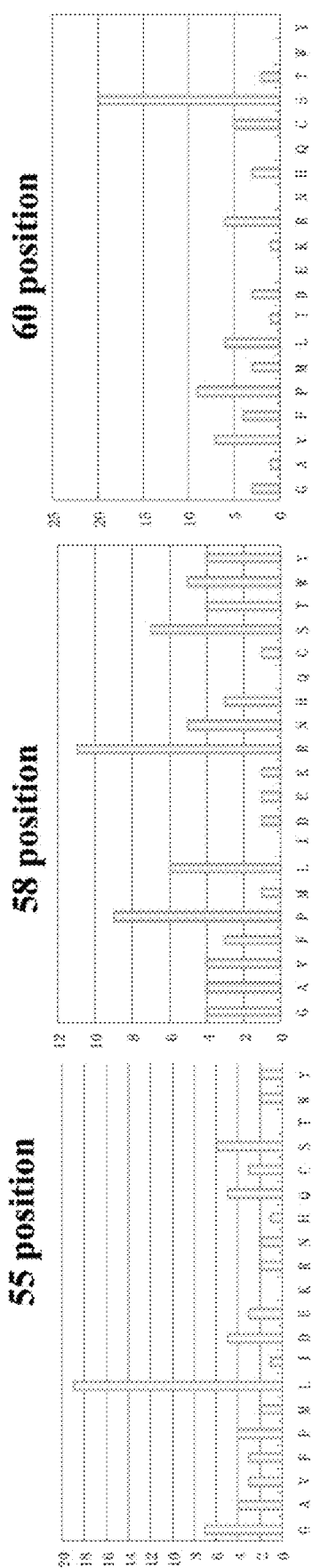
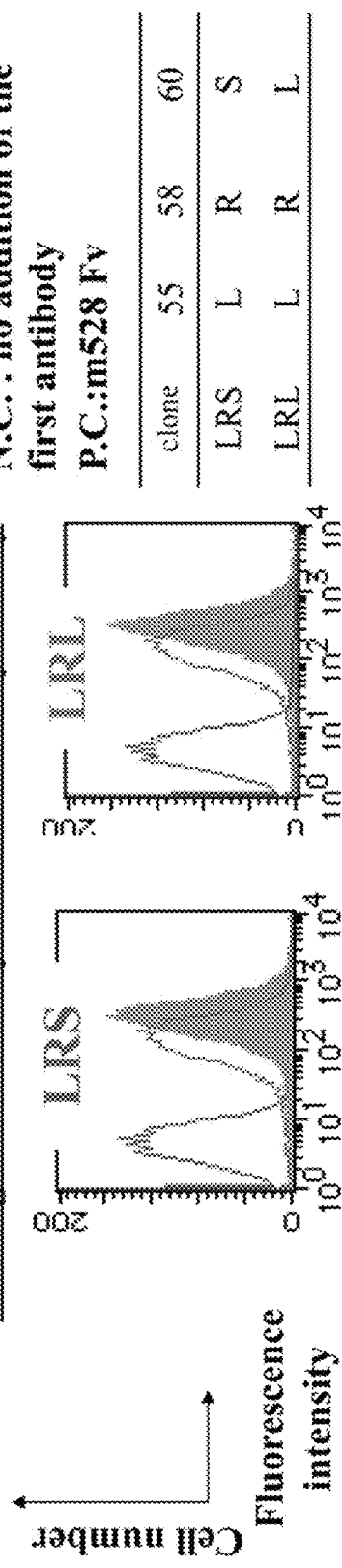

Fig.11

| | $K_A \times 10^7$ [1/M] | $\Delta G$ [kJ/mol] | $\Delta H$ [kJ/mol] | $T\Delta S$ [kJ/mol] |
|---|---|---|---|---|
| m528 Fv | 81.7 | -50.9 | -80.0 | -29.1 |
| 2HH11 | 61.8 | -50.4 | -74.4 | -24.0 |
| h528 Fv | 2.1 | -41.8 | -78.6 | -36.8 |
| LRS | 105.2 | -51.5 | -108.7 | -57.2 |
| LRL | 410.0 | -54.8 | -99.9 | -45.1 |

US 8,921,525 B2

HIGHLY-FUNCTIONAL MUTANT OF HUMANIZED ANTI-EGFR ANTIBODY VARIABLE REGION

FIELD OF THE INVENTION

The present invention is related to a humanized variable region of a heavy chain (h5H) or a light chain (h5L) of an anti-human epithelial cell growth factor (EGF) receptor 1 antibody 528 wherein the variable regions have amino acid mutation, and to various kinds of antibody molecules comprising the regions.

BACKGROUND OF THE INVENTION

Recently, immunotherapy has been used as a safe therapy for the treatment of cancer, rheumatoid, etc. In the immunotherapy of cancer, an antibody showing a cytotoxic activity specifically upon cancer cells is used. While it is recognized that an antibody drug comprising such antibody will show high and safe therapeutic effects with little side effects, it has a problem that it would cost much since said drug needs to be produced by using established animal cells.

As a result, it has been a worldwide trend to produce a low molecular-weight antibody such as a single-chain antibody (scFV) that contains VET and VL of a certain antibody in a single-chain polypeptide. Such low molecular-weight antibody can be economically produced by E. coli. However, it is concerned that its half-life in a body will be decreased due to its low molecular weight, reducing the period of effecting medical benefits. Also, it is a problem that affinity of such low molecular-weight antibody with monovalence is lower than that of a full antibody such as IgG with polyvalence for a target antigen. Furthermore, as a main mechanism of an action of the antibody drug is considered to be an antibody dependent cytotoxic activity (ADCC) via Fc region, it is concerned that the ADCC of the scFv that has no Fc region would be low. Non-Patent Document 1 may be referred to with respect to the scFv.

Accordingly, a bispecific antibody with a low molecular weight has been developed, which can cross-link between cancer cells and immune cells. Only one of such bispecific antibody with a low molecular weight, called "BiTE", which consists of two fragments of scFv linked with each other in tandem, has been now brought into a clinical trial (Science 2008 August 15:321 (5891): 974-7). However, as the BiTE is produced by using animal cells, its production cost and yield have become problematic. Furthermore, it was reported that it was difficult to prepare the tandem scFv-type bispecific antibody with a low molecular weight such as BiTE from soluble fraction of E. coli (J Mol Biol, 2003 330(1):99-111).

Among antibodies with multiple specificities, an antibody with bispecificity (Bispecific Antibody: BsAb) has been studied intensively. The bispecific antibody can bind specifically to two different kinds of antigens so that it will be utilized as a therapeutic agent having a specific anti-cancer effect. A diabody (Db) is a minimum unit of the above bispecific antibody. It was developed by utilizing the property that the variable region in a heavy chain (VH) and the variable region in a light chain (VL) derived from the same parent antibody will form a hetero-dimer through non-covalent bond (Non-Patent Document 2).

The diabody-type bispecific antibody is characterized by having low immunogenicity and high infiltrating activity into tumor tissues due to its low molecular weight (ca. 60,000), and by being able to be easily mass-produced at a low cost with use of microorganisms such as E. coli, and to be easily altered in function by means of genetic engineering.

The present inventors already found that the diabody-type bispecific antibody (Ex3) that was produced by utilizing an anti-human epithelial cell growth factor receptor 1 (Her1) antibody 528 and an anti-CD3 antibody OKT3, and its humanized diabody-type bispecific antibody (referred to as "hEx3" in Patent Document 1) showed extremely strong antitumor effects. It was further speculated that the structural stability of the variable regions of the above antibodies 528 and OKT3 themselves and their combination are very important for showing such advantageous effects by comparison with an diabody-type bispecific antibody prepared using other antibodies.

Furthermore, the present inventors have developed a highly functional bispecific antibody based on said humanized diabody-type bispecific antibody (Patent Document 2).

Methods for the production of bispecific antibodies other than the diabody-type bispecific antibody are described in Non-Patent Documents 3 and 4.

The anti-human epithelial cell growth factor receptor 1 (Her 1) antibody 528 has an effect to inhibit the growth of tumor cells. However, as already described, it is known that when the valency to EGFR is monovalence, the affinity with the antigen will be low and will show only little effect. Actually, no inhibiting effect against tumor cells could be recognized with respect to a single chain antibody (scFV) of the humanized antibody 528. Polymerization of scFV by means of the modification of a linker has been already tried in order to improve the said problem of such scFV (Non-Patent Document 5). Recently, a dimer of scFV was reported to induce apoptosis in lymphoma (Non-Patent Document 6). However, there is no report until now about scFV polymers that will show the growth-inhibiting effect against solid cancers or EGFR-positive cancers.

PRIOR ARTS

Patent Documents

Patent Document 1: Japanese Patent No. 3803790
Patent Document 2: WO 2007/108152 A1

Non-Patent Documents

Non-Patent Document 1: Rosenburg and Moore (Ed.), "The Pharmacology of Monoclonal Antibodies", Vol. 113, Springer-Verlag, New York, pp. 269-315 (1994)
Non-Patent Document 2: Hollinger, et al., Proc. Natl. Acad. Sci. USA 90, 6444-6448, 1993
Non-Patent Document 3: Alt M, et. al. Novel tetravalent and bispecific IgG-like antibody molecules combining single-chain diabodies with the immunoglobulin gamma1 Fc or CH3 region. FEBS Lett., 454, 90-4. (1999)
Non-Patent Document 4: Lu D, et. al. A fully human recombinant IgG-like bispecific antibody to both the epidermal growth factor receptor and the insulin-like growth factor receptor for enhanced antitumor activity. J Biol. Chem., 280, 19665-72. (2005)
Non-Patent Document 5: Biomol. Eng. 2001 18(3): 95-108
Non-Patent Document 6: Biochem Biophysic Res Commun. 2004 315 (4): 912-8

DISCLOSURE OF THE INVENTION

Problem to be Solved by the Invention

The main purpose of the present invention is therefore to provide an antibody that shows more excellent cytotoxic and cell-growth inhibition activities, that is based on the anti-human epithelial cell growth factor (EGF) receptor 1 (Her 1) antibody.

Means for Solving the Problems

The present invention is therefore related to the following aspects:
[1] A mutant of a heavy chain humanized variable region (5H) of an anti-human epithelial cell growth factor (EGF) receptor 1 (Her1) antibody 528 that consists of an amino acid sequence represented by SEQ ID NO:4, or a mutant of a light chain humanized variable region (5L) of an anti-human EGF receptor 1 (Her1) antibody 528 that consists of an amino acid sequence represented by SEQ ID NO:2, which is characterized by having one or a few amino acid mutations within its CDR2.
[2] A mutant of a heavy chain humanized variable region (5H) of an anti-human epithelial cell growth factor (EGF) receptor 1 (Her1) antibody 528 that consists of an amino acid sequence represented by SEQ ID NO:4, which is characterized in that a binding coefficient (Ka) of an Fv antibody comprising said mutant is 8-33 times higher than that of an Fv antibody comprising a heavy chain humanized variable region (5H) of the antibody 528.
[3] A mutant according to Aspect 1 or 2, wherein Tyr 52 of 5H is replaced by Trp.
[4] A mutant according to Aspect 3, wherein Ser 55 is further replaced.
[5] A mutant according to Aspect 4, wherein Ser 55 is replaced by an amino acid selected from the group consisting of Thr, Lys, Arg, Asn and Gln.
[6] A mutant according to Aspect 4 or 5, wherein Lys 63, Lys 65 and/or Asn 66 is further replaced.
[7] A mutant according to Aspect 6, wherein Lys 63 is replaced by Gln.
[8] A mutant according to Aspect 6, wherein Lys 65 is replaced by Gln.
[9] A mutant according to Aspect 6, wherein Asn 66 is replaced by Gln, Lys or Ser.
[10] A mutant according to Aspect 6, wherein Ala 97 is further replaced.
[11] A mutant according to Aspect 10, wherein Ala 97 is replaced by Thr.
[12] A mutant of a light chain humanized variable region (5L) of an anti-human epithelial cell growth factor (EGF) receptor 1 antibody 528 that consists of an amino acid sequence represented by SEQ ID NO:2, which is characterized in that a binding coefficient (Ka) of an Fv antibody comprising said mutant is 50-200 times higher than that of an Fv antibody comprising a light chain humanized variable region (5L) of the antibody 528.
[13] A mutant according to Aspect 1 or 2, wherein Lys 55 of 5L is replaced by Leu, Asp 58 is replaced by Arg, and/or Phe 60 is replaced by Ser or Leu.
[14] An antibody molecule comprising as its constituent the mutant according to any one of Aspects 1-13.
[15] An antibody molecule according to Aspect 14, which is selected from the group consisting of IgG-type antibody molecule, humanized diabody-type bispecific antibody, highly functional bispecific antibody, antibody molecule, and polymerized low-molecular antibody.
[16] An antibody molecule according to Aspect 14 or 15, wherein the light chain humanized variable region (5L) of an anti-human EGF receptor 1 antibody 528, the light chain humanized variable region (OL) of an anti-CD3 antibody OKT3 and the heavy chain humanized variable region (OH) of the anti-CD3 antibody OKT3 consist of an amino acid sequence represented by SEQ ID NOs:2, 6 and 8, respectively.
[17] A single-chain polypeptide constituting the antibody molecule of any one of Aspects 14-16
[18] A nucleic acid molecule encoding the mutant of any one of Aspects 1-13, or the single-chain polypeptide of Aspect 17.
[19] A nucleic acid molecule encoding both of the two kinds of the single-chain polypeptides constituting the antibody molecule of any one of Aspects 14-16.
[20] A replicable cloning vector or an expression vector containing the nucleic acid molecule of Aspects 18 or 19.
[21] The vector of Aspect 20, which is a co-expression vector.
[22] The vector of Aspect 20 or 21, which is a plasmid vector.
[23] A host cell transformed with the vector of Aspect 20 or 21.
[24] A method for the production of the antibody molecule of any one Aspects 14-16, comprising culturing a host cell according to Aspect 23 to express the two kinds of the single-chain polypeptides constituting said antibody molecule, collecting and purifying said single-chain polypeptides, assembling the two kinds of the single-chain polypeptides, and separating and collecting the antibody molecule thus formed.
[25] The method of Aspect 24 wherein the host cell is *E. coli*, and the two kinds of the single-chain polypeptides are collected from supernatant of a culture medium, periplasm fraction, intracellular soluble fraction or intracellular insoluble fraction.
[26] A method for the production of the antibody molecule of any one Aspects 14-16, comprising culturing a host cell transformed with the co-expression vector of Aspect 21 to express the two kinds of the single-chain polypeptides constituting said antibody molecule, allowing the transformed cell to form the diabody-type bispecific antibody in said cell, and separating and collecting the bispecific antibody thus formed.
[27] A pharmaceutical composition comprising the antibody molecule of any one of Aspects 14-16 as an active ingredient.
[28] The pharmaceutical composition of Aspect 27 for use in eliminating, hurting, damaging and/or reducing tumor cells.

Advantages of the Invention

It is confirmed that the mutant of the heavy chain humanized variable region (5H) of an anti-human EGF receptor 1 antibody 528, or the mutant of the light chain humanized variable region (5L) of an anti-human EGF receptor 1 antibody 528, which is characterized by having one or a few (for example, 1-5, or 1-3) amino acid mutations within its region, especially within CDR2, has very excellent cytotoxic and cell-growth inhibition activities.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 9 shows specific amino acid mutations in each VL mutant and the results of their binding evaluation by means of flow cytometry.

FIG. 11 shows the results of thermodynamic analysis of the light chain humanized variable region (5L) of the antibody 528 by means of Isothermal Titration calorimeter.

BEST MODE FOR CARRYING OUT THE INVENTION

The mutant of the heavy chain humanized variable region (5H) or the light chain humanized variable region (5L) of the anti-human EGF receptor 1 (Her 1) antibody 528 is characterized by having one or a few (for example, 1-5, or 1-3) amino-acid mutations in a part exposed to the surface of a solvent within CDR2 of said variable region (5H) consisting of an amino acid sequence represented by SEQ ID NO:4 or within CDR2 of said variable region (5L) consisting of an amino acid sequence represented by SEQ ID NO:2.

The binding coefficient (Ka) of the antibody comprising the above mutant having amino acid mutation(s) in 5H is 8-33 times higher than that of the Fv antibody comprising the heavy chain humanized variable region (5H) of the wild-type antibody 528 (h528 Fv WT).

The binding coefficient (Ka) of the antibody comprising the above mutant having amino acid mutation(s) in 5L is 50-200 times higher than that of the Fv antibody comprising the light chain humanized variable region (5L) of the wild-type antibody 528 (h528 Fv WT).

As an example of the above amino-acid mutation in 5H, there may be mentioned replacement of Tyr 52 by Trp. This example may further include replacement of Ser 55 by an amino acid selected from the group consisting of Thr, Lys, Arg, Asn and Gln. These mutants may further include mutation of Lys 63, Lys 65 and/or Asn 66. For example, Lys 63 and Lys 65 may be replaced by Gln, and Asn 66 may be replaced by Gln, Lys or Ser. Additionally, Ala 97 may be further replaced, for example, by Thr.

As an example of the above amino-acid mutation in 5L, there may be mentioned replacements of Lys 55 by Leu, Asp 58 by Arg, and/or Phe 60 by Ser or Leu.

Various kinds of antibody molecules may be prepared which comprise as their constituent the mutant according to the present invention such as, for example, usual IgG-type antibody molecule, humanized diabody-type bispecific antibody (Patent Document 1), humanized highly functional bispecific antibody (Patent Document 2) and the like.

Specific structures and it preparation method that are comprised in the humanized highly functional bispecific antibody (BsAb) are disclosed in detail in WO 2007/108152 A1 (Patent Document 2).

There is no limitation on the constant region or Fc region comprised in the present antibodies as long as it is derived from the human antibody. For example, CL may be derived from κ or λ chain. Fc region or the heavy chain constant region is usually derived from γ chain of IgG. The amino acid sequences represented by SEQ ID NOS: 29, 30 and 33 disclosed in Patent Document 2 are representative examples of CH1, CH2 & CH3, and CL, respectively.

Figure 3:
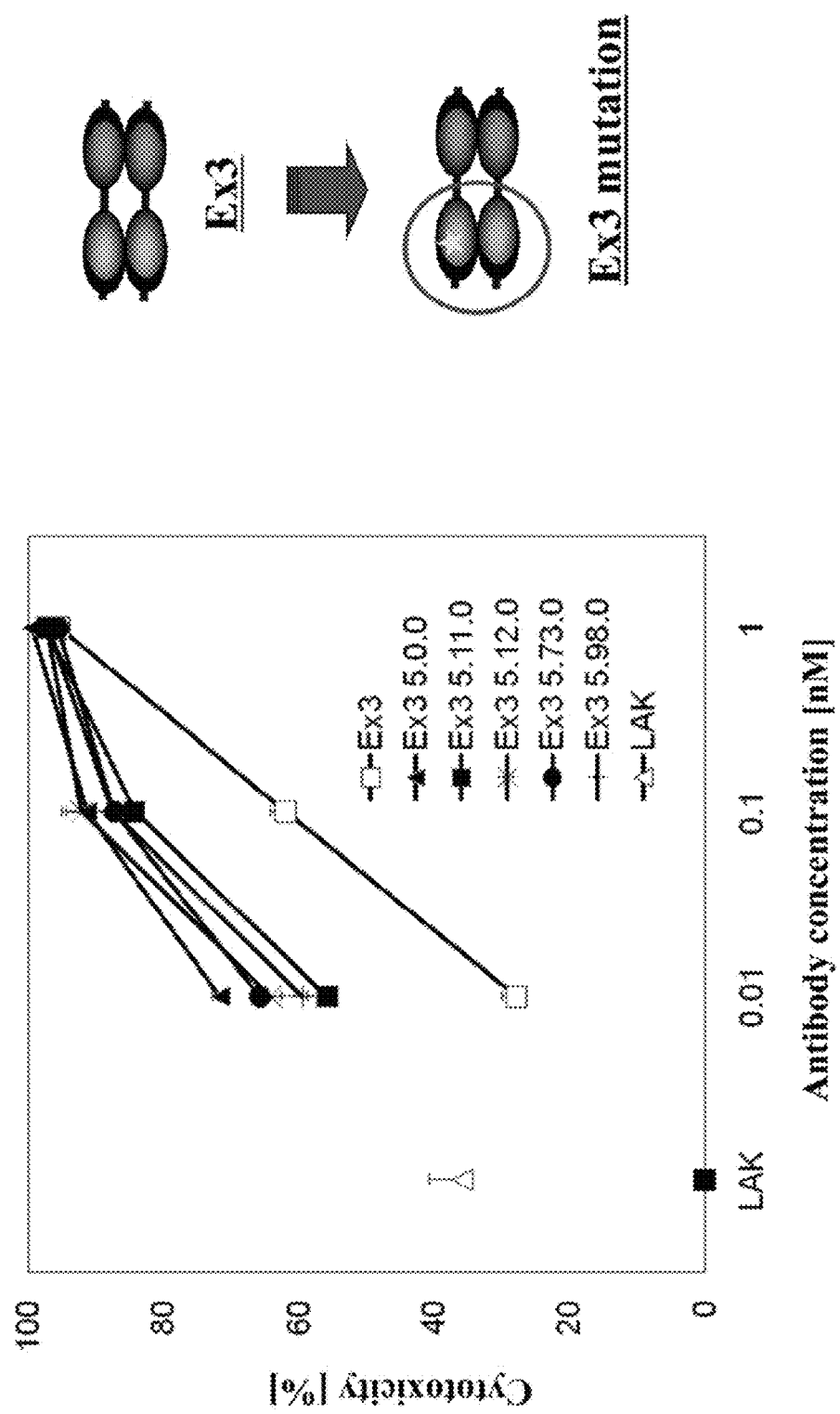
FIG. 3 shows the results of Cytotoxicity Test (cell-growth inhibition test) with the diabody-type bispecific antibody (Ex3 mutant) comprising as its constituent the mutant of a heavy chain humanized variable region (5H) of the antibody 528.
Figure 4:
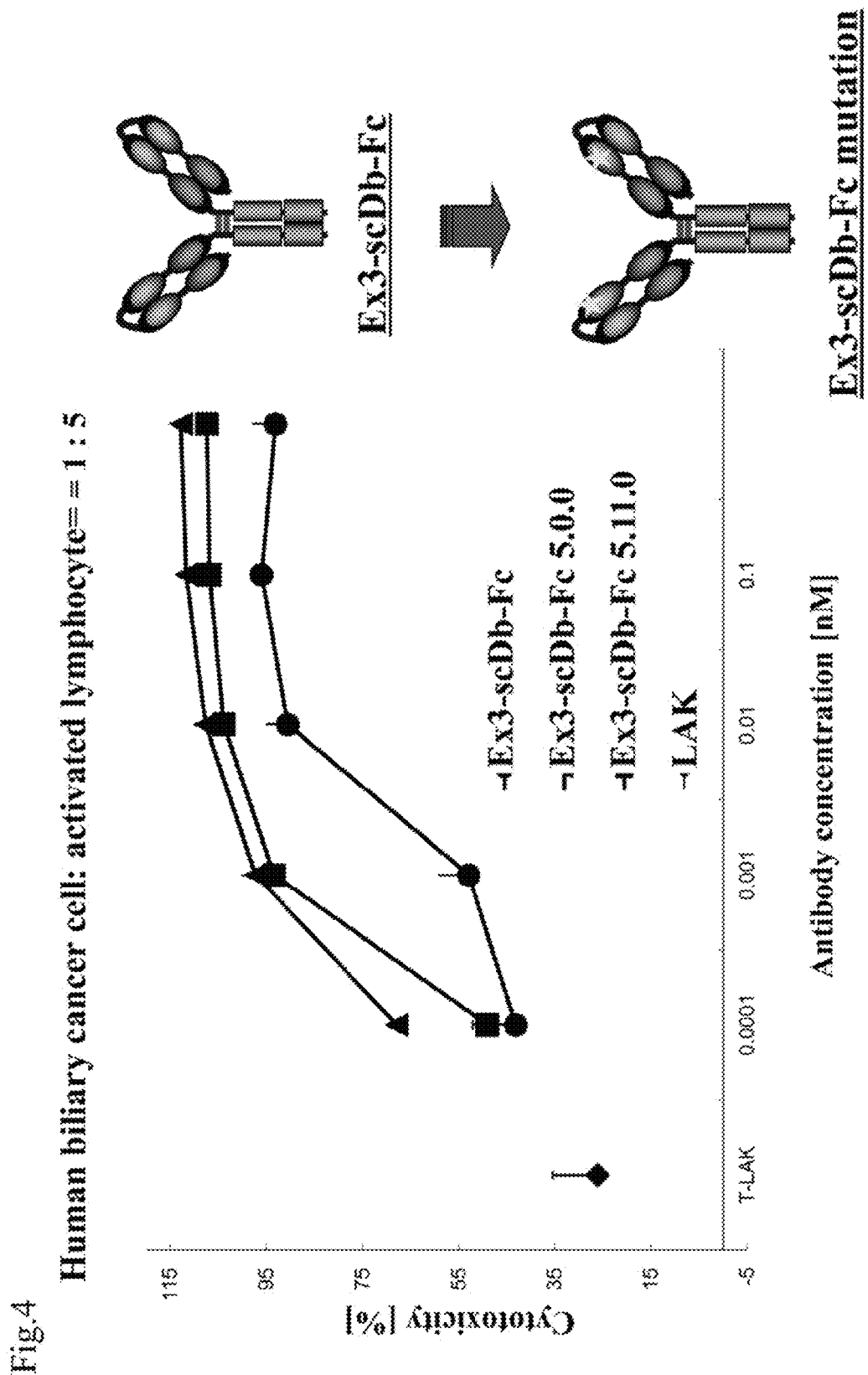
FIG. 4 shows the results of Cytotoxicity Test (cell-growth inhibition test) with the highly functional bispecific antibody (Ex3-scDb-Fc mutant) comprising as its constituent the mutant of a heavy chain humanized variable region (5H) of the antibody 528.

Representative examples of the amino acid sequences of the PreSission sequence, hinge region, peptide linker, signal peptide, etc. that are comprised in the single-chain polypeptides constituting the present antibodies are shown in FIGS. 3-3 and 3-4 of Patent Document 2. The PreSission sequence comprises a protease-cleavage site. There is no limitation on the kind of protease used in the present invention, and any enzyme known in the art such as Thrombin and Factor Xa may be used, and the amino acid sequence comprising the protease-cleavage site may be optionally selected.

Furthermore, the present invention include the humanized diabody-type bispecific antibody, humanized highly functional bispecific antibody wherein a light chain variable region is located at the N-terminal side of a heavy variable region (LH type) in each polypeptide constituting said antibodies.

The polymerized low-molecular antibody are constituted by aggregation of a plurality (for example 2-4) of a single-chain antibody (scFv) comprising the mutant of the heavy chain humanized variable region (5H) and/or the light chain humanized variable region (5L) the anti-human EGF receptor 1 antibody 528. The above heavy chain humanized variable region (5H) and the light chain humanized variable region (5L) are in each single chain linked via a peptide linker consisting of 1-9 amino acids. Each single-chain antibody may lack one or a few amino acids that are located at C-terminus of the humanized variable region of N-terminal side, or at N-terminus of the humanized variable region of C-terminal side.

Mouse B cell hybridoma 528 producing the anti-EGFR antibody (ID:TKG0555) is deposited in Cell Resource Center for Biomedical Research, Institute of Development, Aging and Cancer of TOHOKU University. The above hybridoma 528 producing anti-EGFR antibody is also stored at ATCC with an ATCC Accession No. HB-8509, so that it may be obtained from these deposit authorities.

On the other hand, the anti-CD3 antibody, OKT3 (ID: TKG0235) is deposited in Cell Resource Center for Biomedical Research, Institute of Development, Aging and Cancer, of TOHOKU University, and is also stored at ATCC with an ATCC Accession No. CRL-8001, so that it may be obtained from these deposit authorities.

cDNA may be prepared by known methods. For example, mRNA is extracted with ISOGEN (Nippon Gene Co.) and then cDNA is prepared by means of First-Strand cDNA Synthesis Kit (Amersham Biosciences Co.). PCR reaction is done for the cDNA using cloning primers that are synthesized in accordance with the disclosure of a Reference document (Krebber, A. et al. Reliable cloning of functional antibody variable domains from hybridomas and spleen cell repertoires employing a reengineered phage display system. J Immunol Methods 201, 35-55. (1997)) so as to determine the sequences of the variable regions of H and L chains of each antibody.

The term "humanized" variable region as used in the single-chain polypeptide constituting the mutant of the variable region or the antibody means a human immunoglobulin (a recipient antibody) in which at least a part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in either the recipient antibody or the introduced CDR or framework. These changes are made in order to optimize or improve the properties of the resulting antibody. More detailed information on these changes are referred to Jones et al., Nature 321, 522-525 (1986); Reichmann et al., Nature 332, 323-329 (1988); EP-B-239400; Presta, Curr. Op. Struct. Biol 2, 593-596 (1992); and EP-B-451216.

The humanized variable region of the antibody may be prepared in accordance with any methods known to those skilled in the art, for example, by analyzing various conceptual humanized preparations based on three-dimensional immunoglobulin models of the recipient antibody and donor antibody, and analyzing them. The three-dimensional immunoglobulin models are well known in the art, being referred to, for example, WO92/22653.

Thus, one example of the humanized variable region according to the present invention is an antibody wherein the complementary determining regions (CDR) in the variable regions are derived from a mouse antibody, and the other parts are derived from a human antibody.

The activity or function of the resulting antibody may be deteriorated due to the humanization. The activity or function of the diabody-type bispecific antibody according to the present invention may be therefore improved by being provided with a site-specific mutation at an appropriate position in the single-chain polypeptide, for example, at a position in the framework which can affect the CDR structure, such as in canonical sequence or vernier sequence.

Specifically, the humanization of the variable regions of 528 was performed by means of CDR grafting. Thus, a human antibody having FR (Frame Work) with the highest homology was screened and selected by a homology search in view of the length of each CDR and the like. An amino acid sequence was designed, in which the CDR of the selected human antibody was replaced with CDR of 528. The total gene may be then synthesized by means of overlapping PCR by preferably using the optimum codons for E. coli.

It was already reported that the variable region of the humanized OKT3 could maintain its activity when compared with the mouse OKT3 (Adair, J. R. et al. Humanization of the murine anti-human CD3 monoclonal antibody OKT3. Hum Antibodies Hybridomas 5, 41-7. (1994)). The total gene was synthesized by means of overlapping PCR based on the amino acid sequence of the variable regions of the humanized OKT3 disclosed in the above document. The optimum codons for E. coli were used in the synthesis. It was also reported that the use of the gene containing the optimum codons would increase the expression level in E. coli.

The humanized variable region of the light chain (5L) and the humanized variable region of the heavy chain (5H) of the anti-human EGF receptor 1 antibody 528, and the humanized variable region of the light chain (OL) and the humanized variable region of the heavy chain (OH) of the anti-CD3 antibody OKT, which are comprised in the single-chain polypeptides that constitute the antibody molecule of the present invention may have a nucleotide sequence and an amino acid sequence represented by SEQ ID NOS:1 and 2, 3 and 4, 5 and 6, and 7 and 8, respectively.

It is preferred that the humanized variable regions of the light chain (VL) and the heavy chain (VH) are linked via an appropriate peptide linker. Any linker known in the art or one modified therefrom may be optionally selected and used in the present invention as long as it makes hard for the single-chain polypeptide to interact within its molecule so that it will enable the formation of a polymer of plurality of the single-chain antibodies. As a result, the VH and VL derived from different single-chain antibodies with each other shall assemble appropriately so as to form a structure that mimics or improves the function of an original protein (the function originated or derived from the original polypeptide or protein) such as all or part of its biological activity. The peptide linker according to the present invention may have about 1-20 amino acids, preferably about 1-15 amino acids, more preferably about 2-10 amino acids.

Alternatively, the two humanized variable regions may be directly linked with each other in the single-chain polypeptide. In such case, one or a few amino acids located at C-end of the humanized variable regions of the N-terminal side, or one or a few amino acids located at N-end of the humanized variable regions of C-terminal side are deleted in order to increase three-dimensional degree of freedom in each single-chain antibody and to improve their polymerization.

The polypeptide having an amino acid sequence in which one or a few (for example, 1-5, or 1-3) amino acids are substituted, deleted, inserted or added in the amino acid sequences represented by the above SEQ ID NOS, and having substantially the same property and function as that of the original polypeptide such as an antigen specificity as that of its variable region may be also used as the single-chain polypeptide constituting the present antibody molecule. However, the amino acid mutation in SEQ ID NO:4 of the present mutant shall be maintained. It is preferable to make a substitution among amino acids belonging to the same group (polar, non-polar, hydrophobic, hydrophilic, positive-charged, negative-charged, or aromatic amino acid group), or to make a deletion or addition of amino acid so as not to cause a substantial difference or effects with respect to the three-dimensional or local charge-condition of the protein. Such polypeptides having the substitution, deletion or addition of the amino acid(s) my be easily prepared by well known methods such as site-specific mutation (point mutation method or cassette mutation), genetic homologous recombination, primer extension method and PCR, or any optional combinations thereof. The above amino acid sequence comprising one or few amino acids that are substituted, deleted, inserted or added have homology (identity) of 90% or more, preferably 95% or more, more preferably 99% or more with a full-length amino acid sequence in the original amino acid sequence.

The representative examples of the nucleic acid molecules (oligonucleotides) encoding the whole or part of the amino acid sequences of the single-chain polypeptide comprised in the mutant or antibody molecule according to the present invention have the nucleotide sequences shown in the above SEQ ID NOS. Furthermore, as a nucleic acid molecule with the nucleotide sequence having homology of 90% or more, preferably 95% or more, more preferably 99% or more with a full-length nucleotide sequence represented by the same SEQ ID NOS are considered to encode a polypeptide having substantially the same property and function as that of the original polypeptide or part thereof, the above nucleic acid molecule is included in the nucleic acid molecule of the present invention. Although the nucleic acid molecule comprises a nucleotide sequence encoding at least either of the two kinds of the single-chain polypeptides constituting the antibodies such as diabody-type bispecific antibody according to the present invention, it preferably comprises two kinds of nucleotide sequences together, each of which encodes one of the two kinds of said single-chain polypeptides, respectively.

In order to determine the homology between two amino acid or nucleotide sequences, they may be preliminarily treated into an optimum condition for comparison. For example, a gap may be inserted into one of the sequences to optimize the alignment with the other sequence, followed by the comparison of amino acid or nucleotide at each site. When the same amino acid or nucleotide exists at a corresponding site of the first and second sequences, these two sequences are considered to be identical with respect to said site. Homology between two sequences is shown by a percent ratio of the number of the identical sites over the total number of amino acids or nucleotides between the two sequences.

The term "homology" in this specification means an amount (or a number) of the amino acids in an amino acid sequence or the nucleotides in a nucleotide sequence, which are determined to be identical with each other in the relationship between two sequences, showing an extent of the correlation between the two polypeptide or nucleotide sequences. The homology may be easily calculated. The term "homology" or "identity" is well known in the art, and many methods for the calculation of such homology are known, among them. For example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991). A general method for the determination of the homology between two sequences is disclosed, for example, in Martin, J. Bishop (Ed.), Guide to Huge Computers, Academic Press, San Diego, (1994); Carillo, H. & Lipman, D., SIAM J. Applied Math., 48: 1073 (1988). A preferable method for the determination of the homology between two sequences is, for example, one designed to obtain a largely related part between said two sequences. Some of them are provided as a computer program. Preferable examples of the computer programs for the determination of the homology between two sequences include GCG program package (Devereux, J. et al., Nucleic Acids Research, 12(1): 387 (1984)), BLASTP, BLASTN, FASTA (Atschul, S. F. et al., J. Molec. Biol., 215: 403 (1990).

The nucleic acid of the present invention further includes a DNA molecule that hybridizes with a DNA comprising a nucleotide sequence complementary to the nucleotide sequence represented by the above SEQ ID NOS under stringent conditions, and encodes a polypeptide having substantially the same property and function as that of the polypeptides represented by the above SEQ ID NOS.

Hybridization may be carried out by or in accordance with a method well known in the art such as that described in Molecular cloning third. ed. (cold Spring Harbor Lab. Press, 2001). Hybridization may be done in accordance with an instruction or manual attached to a commercially available library.

Hybridization may be carried out by or in accordance with a method well known in the art such as that described in Current protocols in molecular biology edited by Frederick M. Ausbel et al., 1987). Hybridization may be done in accordance with an instruction or manual attached to a commercially available library.

The phrase "stringent conditions" in this specification may be defined by a suitable combination of salt concentration, organic solvent (for example, formamide), temperature, and other known conditions. Thus, stringency will be increased by the decrease of salt concentration, or the increase of an organic solvent concentration or hybridization temperature. The washing conditions after the hybridization may also affect the stringency. The washing conditions are also defined by salt concentration and temperature. The stringency of washing will be increased by the decrease of salt concentration or the increase of temperature.

Accordingly, the "stringent conditions" in this specification means conditions under which a specific hybrid can be formed only between the nucleotide sequences having homology of about 80% or more, preferably about 90% or more, more preferably about 95% or more on a total average. Specifically, they may be sodium concentration of 150-900 mM, preferably 600-900 mM, pH6-8 at 60-68° C. One example of the stringent conditions is hybridization in 5×SSC (750 mM NaCl, 75 mM $Na_3$ Citirate), 1% SDS, 5×Denhardt solution 50% formaldehyde at 42° C., followed by the washing with 0.1×SSC (15 mM NaCl, 1.5 mM $Na_3$ Citirate), 0.1% SDS at 55° C.

Furthermore, the nucleic acid encoding the humanized variable regions in the single-chain polypeptide of the present invention may be synthesized by means of an over-lapping PCR method based on a pre-determined amino acid sequence. The nucleic acid used herein has no limitation in its chemical structure or preparation route, as long as it is a molecule encoding the single-chain polypeptide, including gDNA, cDNA chemically-synthesized DNA and mRNA.

Specifically, the nucleic acid according to the present invention may be isolated from cDNA library by means of hybridization or PCR based on the sequences disclosed in literatures. The thus isolated DNA may be inserted in an expression vector, with which a host cell such E. coli, COS cell, CHO cell or myeloma not expressing immunoglobulin are transfected to synthesize a monoclonal antibody in the thus transformed host cells. PCR may be carried out in accordance with a method known in the art, or substantially the same or altered methods. The methods disclosed in, for example, R. Saiki, et al., Science, 2301350, 1985; R. Saiki, et al., Science, 239:487, 1988; H. A. Erlich ed., PCR Technology, Stockton Press, 1989; D. M. Glover et al., ed., "DNA Cloning," $2^{nd}$. ed., Vol. 1, (The Practical Approach Series), IRL Press, Oxford University Press (1995); M. A. Innis et al., ed., "PCR Protocols: a guide to methods and applications," Academic Press, New York (1990); M. J. McPherson, P. Quirke and G. R. Taylor (Ed.), PCR: a practical approach, IRL Press, Oxford (1991); M. A. Frohman e al., Proc. Natl. Acad. Sci. USA, 85, 8998-9002 (1988), and their modified and altered methods may be used in the present invention. PCR may be performed with use of a commercially available kit in accordance with manufacturer's protocols.

The sequencing method of nucleic acids such as DNA may be referred to Sanger et al., Proc. Natl. Acad. Sci. USA 74:5463-5467 (1977). A general method for recombinant DNA techniques may be referred to J. Sambrook, E. F. Fritsch & T. Maniatis (ed.), "Molecular Cloning: A Laboratory Manual (2nd edition)", Cold Spring Harbor Laboratory Press, Cold Spring Harbor, N.Y. (1989) and D. M. Glover et al. (ed.), $2^{nd}$ ed., Vol. 1 to 4 (The Practical Approach Series), IRL Press, Oxford University Press (1995).

The nucleic acid encoding the single-chain polypeptide constituting the present antibody molecule or each region contained therein may be modified or altered so that it will optionally encode a desired peptide or amino acid depending on the purpose. The techniques for such modification or alternation are disclosed in Mutagenesis: a Practical Approach, M. J. McPherson (ed.), IRL Press, Oxford, UK (1991), including a site-specific mutagenesis introduction method, cassette mutagenesis induction method and PCR mutagenesis method.

The term "modification (or alternation)" as used herein refers to insertion, deletion or substitution of base(s) in at least one codon encoding an amino acid residue in the originally obtained nucleic acid. It includes alternation of the amino acid sequence per se of the single-chain polypeptide by replacing a codon encoding the original amino acid with a codon encoding another amino acid.

Alternatively, the nucleic acid encoding the single-chain polypeptide may be altered without changing the amino acid per se, by using a codon suitable for a host cell such as $E.\ coli$ (an optimum codon). With the use of the optimum codon, expression efficiency of the single-chain polypeptide in the host cell will be improved.

The antibody molecule according to the present invention may be produced by various methods well known in the art such as genetic engineering technique and chemical synthesis. For example, the genetic engineering technique includes producing a replicable cloning vector or an expression vector containing the nucleic acid molecule encoding each of the two kinds of the single-chain polypeptides constituting the above bispecific antibody, transforming a host cell with the vector, culturing the transformed host cell to express each of the single-chain polypeptides, collecting and purifying said single-chain polypeptides, assembling the two kinds of the single-chain polypeptides, and separating and collecting the bispecific antibody thus formed.

The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which can not be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium. Furthermore, various peptide tags (c-myc and His-tag, for example) known in the art may be contained at its end, etc.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell.

Any cell known in the art may be used as the host cell, for example, there may be mentioned prokaryotic cells such as including $E.\ coli.$, eukaryotic cells such as mammalian cells such Chinese hamster ovary (CHO) cell and human cells, yeast, and insect cells. For example, BL21 star (DE3) strain is cultured in 2×YT culture medium at about 28° C. and induced with IPTG of about 0.5 mM, so that the yield of the present antibody molecule may be highly improved so as to increase its production efficiency.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such ethanol, a dissolving agent such as guanidine hydrochloride and urea. The present antibody molecule is produced by assembling or rewinding the two kinds of the single-chain polypeptides thus purified, and separating and collecting the thus formed antibody molecule.

Assembling treatment will bring a single-chain polypeptide back in its appropriate spatial arrangement in which a desired biological activity is shown. Since this treatment may also bring polypeptides or domains back into their assembling state, it may be considered "re-assembling." It may be also called "re-constitution" or "refolding" in view of gaining the desired biological activity. The assembling treatment may be carried out by any method known in the art, preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the present highly functional BsAb thus formed may be done by any method known in the art as well.

As already described above, the antibody molecule according to the present invention may be prepared from the supernatant of a culture medium, periplasm fraction, intracellular soluble fraction and intracellular insoluble fraction.

It is possible to transform a host cell with the co-expression vector containing a nucleic acid molecule encoding both of the two kinds of the single-chain polypeptides constituting the antibody molecule of the present invention, or with the two kinds of a expression vector containing a nucleic acid molecule encoding each of the two kinds of said single-chain polypeptides, respectively, culturing the transformed host cell so as to express the two kinds of the single-chain polypeptides, allowing the transformed cell to form the LH-type bispecific antibody in said cell, and separating and collecting it from supernatant of the culture medium or intracellular soluble fraction. In such case, the above assembling or rewinding treatment is unnecessary so that a high productivity can be achieved at a low cost.

Furthermore, it is preferable to culture BL21 star (DE3) strain (Invitrogen) as a host cell in 2×YT culture medium with shaking at 28° C. overnight, to induce with IPTG at a final concentration of 0.5 mM when O.D at 600 nm becomes about 5, and to collect the desired protein 16 hours later of the induction from the supernatant of the culture medium and periplasm fraction after an osmotic pressure treatment.

A pharmaceutical preparation according to the present invention comprises an active ingredient selected from the group consisting of the present antibody molecule, the single-chain polypeptide, the nucleic acid, the vector, and the host cell described in the above. As shown by the examples in the present specification, since the active ingredient has an activity of eliminating, hurting, damaging and/or reducing tumor cells expressing EGFR in vitro and in vivo, the present pharmaceutical preparation is used as an anti-tumor agent.

An effective amount of the active ingredient may be optionally determined by those skilled in the art depending on the purpose of treatment, medical conditions of a patient to be treated such as kind, site or size of tumor, and administration route. A typical dose or daily dose may be first determined in vitro by using an assay method of growth or existence of the tumors known in the art, then determined with use of such an appropriate animal model as to allow extrapolation of the resulting dose range to human patients.

The pharmaceutical preparation of the present invention may optionally comprise various kinds of pharmaceutically acceptable components known in the art such as carrier, excipient, buffer, stabilizing agent and the like, depending on various factors such as the kind of the active ingredients, its formulation form, the route and purpose of administration, medical conditions of patient.

The pharmaceutical preparation of the present invention may be formulated into any form such as pill, liquid, powder, gel, air spray, microcapsule, and colloidal dispersion (liposome, micro emulsion, etc.).

The pharmaceutical preparation may be administered by injecting or infusing intraveneously, intraperitoneally, intracerebrally, intraspinally, intramuscularly, intraocularly, intraarterially, especially intrabiriarily, or via diseased tissue, or with use of a constant releasing agent system. The active ingredient according to the present invention may be administered through continuous fluid infusion or massive injection. The pharmaceutical preparation according to the present invention is preferably administered in combination with the cell having phagocytosis or cytotoxic activity. Alternatively, the active ingredient such as the present BsAb may be mixed with the above cells so as to bind to them before its administration.

The constant releasing agent generally refers to a formulation that can release the active ingredient of the present invention for a certain period of time. One of the preferred constant releasing agents comprises a semipermeable carrier of solid hydrophobic polymer such as protein, which is shaped into a form such as film or micro capsule.

The pharmaceutical preparation according to the present invention may be produced by a method that is optionally selected from, for example, "Guide Book of Japanese Pharmacopoeia", Ed. of Editorial Committee of Japanese Pharmacopoeia, Version No. 13, published Jul. 10, 1996 by Hirokawa publishing company The terms as used in the present specification and drawings are based on IUPAC-IUB Commission on Biochemical Nomenclature or on meanings of the terms conventionally used in the art.

The present invention will be explained in more detail by referring to the Examples, which are provided only for describing the specific embodiments of the present invention, but not for limiting the scope of the present invention. It is therefore to be understood that various embodiments based on the inventive concept of the present specification may be practiced within the scope of the present invention.

The following examples were or can be carried out with standard techniques well known to those skilled in the art unless otherwise described. Thus, unless otherwise described, specific procedures and treating conditions are in accordance with J. Sambrook, E. F. Fritsch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to 4, (The Practical Approach Series), IRL Press, Oxford University Press (1995) (DNA cloning), and with H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990) (PCR). A commercially available agent and kit were used in accordance with protocols attached thereto.

EXAMPLE 1

Production of a Mutant of a Heavy Chain Humanized Variable Region (5H) of an Anti-Human EGF Receptor 1 (Her1) Antibody 528

Figure 1:
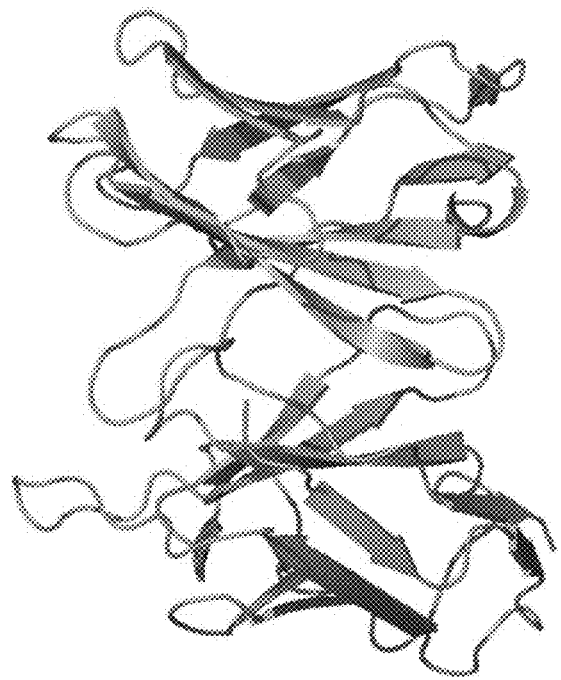
FIG. 1 shows crystal structure of a fragment of the variable region of the humanized antibody 528.

The crystal structure of the humanized antibody 528 was first determined by means of Molecular Replacement method. The results are shown in Table 1 and FIG. 1. Based on the structure thus obtained, mutations were introduced randomly within and in the vicinity of the CDR of the heavy chain humanized variable region (5H) of the anti-human EGF receptor 1 antibody 528 by means of a known Site-Specific Mutagenesis (Site-Directed Mutagenesis) while taking solvent-contacting residues into account. Phages expressing and displaying each VH mutant thus obtained were positive- and negative-selected by means of phage-display method using the transformed CHO cells expressing and displaying EGFR, and CHO cells, respectively. Specific amino acid mutations (underlined) in the resulting mutant VH (designated as "5.0.0", "5.11.0" and the like), and an amino acid sequence of the heavy chain humanized variable region of the antibody 528 represented by SEQ ID NO:4 and the location of each CDR are shown in Table 2 and Table 3, respectively.

TABLE 1

Determination of the crystal structure by means of Molecular Replacement method
Crystallographic Data

|  | Humanized 528 | Mouse 528 |
|---|---|---|
| Space group | P6₅ | P6₂ |
| Unit cell dimension (Å) | a = b = 63.28 | a = b = 126.60 |
|  | c = 225.34 | c = 68.28 |
| Resolution (Å) | 2.1 | 2.3 |
| R factor | 0.27 | 0.19 |
| Free R factor | 0.30 | 0.23 |

TABLE 2 introduction site of mutation

| | CDR2 | Three residues upstream of CDR3 |
|---|---|---|
| h528Fv WT | NIYPGSGGTNYAEKFKN | CAR |
| h528Fv 5.0.0 | NI<u>W</u>PGSGGTNYAEKFKN | CAR |
| h528Fv 5.11.0 | NI<u>W</u>PG<u>T</u>GGTNYAEKF<u>QQ</u> | CAR |
| h528Fv 5.12.0 | NI<u>W</u>PG<u>K</u>GGTNYAEKF<u>QK</u> | CAR |
| h528Fv 5.73.0 | NI<u>W</u>PG<u>N</u>GGTNYAE<u>Q</u>FK<u>Q</u> | CAR |
| h528Fv 5.98.0 | NI<u>W</u>PG<u>Q</u>GGTNYAEKFK<u>S</u> | CAR |
| h528Fv 5.11.T | NI<u>W</u>PG<u>T</u>GGTNYAEKF<u>QQ</u> | C<u>T</u>R |

Table 3

VH
Sequence of the heavy chain variable region of the wholly synthesized humanized 528

```
        10         20         30         40         50         60
CAGGTGCAACTGGTTCAGAGCGGCGCGGAAGTGAAAAAGCCGGGCGCGTCGGTTAAAGTG
 Q  V  Q  L  V  Q  S  G  A  E  V  K  K  P  G  A  S  V  K  V 70         80         90        100  CDR1  110        120
AGCTGCAAAGCCTCAGGCTATACCTTTACGAGCTACTGGATGCATTGGGTGCGCCAGGCC
 S  C  K  A  S  G  Y  T  F  T  S  Y  W  M  H  W  V  R  Q  A 130        140        150        160        170  CDR2  180
CCGGGTCAGGGCCTGGAATGGATGGGTAACATTTATCCGGGCAGCGGTGGCACCAACTAT
 P  G  Q  G  L  E  W  M  G  N  I  Y  P  G  S  G  G  T  N  Y 190        200        210        220        230        240
GCGGAAAAATTTAAGAACCGCGTGACCATGACGCGTGATACCAGCATTTCGACGGCCTAT
 A  E  K  F  K  N  R  V  T  M  T  R  D  T  S  I  S  T  A  Y 250        260        270        280        290  CDR3  300
ATGGAACTGAGCCGCCTGCGTAGCGATGACACCGCCGTGTATTACTGCGCGCGCAGTGGC
 M  E  L  S  R  L  R  S  D  D  T  A  V  Y  Y  C  A  R  S  G 310        320        330        340        350
GGTCCGTATTTTTTCGATTACTGGGGCCAGGGTACGCTGGTTACCGTGAGCTCG (SEQ ID NO: 3)
 G  P  Y  F  F  D  Y  W  G  Q  G  T  L  V  T  V  S  S  (SEQ ID NO: 4)
```

An Fv co-expression vector of each mutant VH and the light chain humanized variable region (VL) of the 528 antibody was constructed. It was crudely purified from the culture supernatant of transformed E. coli BL21 strain by means of metal chelate affinity chromatography, subjected to gel filtration chromatography, and then to cation-exchange chromatography for a final purification. The yield of the purified Fv antibody was about 1-10 mg per 1 L of culture medium.

The resulting mutants were then subjected to thermodynamic analysis by means of Isothermal Titration calorimeter. A target antigen, soluble EGFR, was prepared by another CHO cell expression system and purification with metal chelate affinity chromatography. The thus purified EGFR at a concentration of 5 μM was added to a titration cell, and the mutant Fv at a concentration of 50 μM was then dropped with time. Binding enthalpy (ΔH) and binding coefficient (Ka) were calculated from the change of calorie during the above titration. Free Energy Change (ΔG) and Binding Entropy Change (ΔS) were then calculated from the above values. The results are shown in Table 4. It was confirmed by these results that the binding coefficient (Ka) of the Fv antibodies comprising the above mutants has been increased up to 8-33 times larger than that of an Fv antibody (h528Fv WT) comprising the heavy chain humanized variable region (5H) of the wild type 528 antibody.

TABLE 4

Evaluation of antigen-binding activity of h528 mutants

|  | $Ka \times 10^7$ [$M^{-1}$] | ΔG [kJ/mol] | ΔH [kJ/mol] | TΔS [kJ/mol] |
|---|---|---|---|---|
| h528Fv WT | 1.9 | −41.5 | −61.1 | −19.5 |
| h528Fv 5.0.0 | 14.9 | −46.7 | −87.9 | −41.2 |
| h528Fv 5.11.0 | 61.8 | −50.4 | −74.4 | −24.0 |
| h528Fv 5.12.0 | 44.2 | −49.5 | −69.9 | −20.4 |
| h528Fv 5.73.0 | 49.5 | −49.8 | −71.3 | −21.5 |
| h528Fv 5.98.0 | 50.5 | −49.9 | −76.8 | −26.9 |
| h528Fv 5.11.T | 52.4 | −49.7 | −83.5 | −33.8 |

EXAMPLE 2

Production of an Antibody Molecule Comprising as its Constituent the Mutant of a Heavy Chain Humanized Variable Region (5H) of an Anti-Human EGF Receptor 1 (Her1) Antibody 528

An IgG antibody comprising as its constituent each mutant VH produced in Example 1 was produced as follows.

First, each mutant VH was substituted for the VH site of a humanized 528 IgG expression vector to give an expression vector of a mutant of the humanized 528 IgG. It was then transiently expressed in human embryo kidney cell (HEK) and purified with Protein A column chromatography. The yield of purified antibody was about 1 mg of per 1 L of the culture medium.

A mutant of the humanized diabody-type bispecific antibody (Ex3), comprising as its constituent each mutant VH produced in Example 1, was then produced according to the method disclosed in Patent Document 1. The yield of purified antibody was about 1 mg of per 1 L of the culture medium.

Similarly, a mutant of the highly functional bispecific antibody (Ex3-scDb-Fc), comprising as its constituent each mutant VH produced in Example 1, was produced according to the method disclosed in Patent Document 2. The yield of purified antibody was about 1 mg of per 1 L of the culture medium.

EXAMPLE 3

Production of an LH-Type Highly Functional Bispecific Antibody

An LH-type highly functional bispecific antibody comprising as its constituent each mutant VH produced in Example 1 was produced as follows.

Expression vectors for the LH-type highly functional bispecific antibodies (Ex3-scDb-Fc) were constructed in accordance with the methods disclosed in Example 1 of Patent Document 2 (the first type to the third type) using their sequences and appropriate primers, and the above Ex3-scDb-Fc was prepared in accordance with Example 2 of Patent Document 2 using CHO cells as a host cell. In this production of the LH-type highly functional bispecific antibodies (the first type in Patent Document 2: LH-type Ex3-scDb), however, (OL5H) was first introduced into upstream of (5LOH) via a peptide linker to give Ex3 scDb having the structure of (N-terminal) (OL5H)-(Peptide linker)-(5LOH)(C-terminal), and the mutant of the LH-type Ex3-scDb-Fc was then produced. The yield of purified antibody was about 1 mg of per 1 L of the culture medium.

EXAMPLE 4

Production of a Polymerized Low-Molecular Antibody

The polymerized low molecular antibody (dimer) was prepared as follows. This antibody consisted of a single-chain antibody (scFv) comprising each mutant VH but having a peptide linker removed therefrom.

An expression vector was constructed based on the humanized diabody expression vector (pRA-h5HhOL, pRA-hOHh5L: Japanese Patent No. 380790) targeted for EGFR and CD3. Thus, each vector was digested with a restriction enzyme NcoI and EagI, and the sites of h5H and hOH were exchanged with each other to give a humanized 528scFv expression vector (pRA-h5Hh5L(G1)) having 5-amino acid linker (GGGGS). A c-myc peptide tag and His-tag (Hisx6: histidine hexamer tag) had been introduced tandem into its C-terminal for detection and purification, respectively.

Furthermore, the polymerized low molecular antibody (trimer) was prepared as follows. This antibody consisted of a single-chain antibody (scFv) comprising each mutant VH but having a peptide linker removed therefrom.

The humanized 5H (h5H) and the humanized 5L (h5L) were amplified using A-B primers and C-D primers, respectively. The resulting PCR products were mixed with each other and further amplified using A-D primers. The resulting PCR product was digested with the restriction enzymes NcoI and SacII, and inserted into pRA vector to produce an expression vector (pRA-h5Hh5L(HLG0)) for a VH-VL type humanized 528scFv without a linker.

On the other hand, the h5L and the h5H were amplified using E-F primers and G-H primers, respectively. The resulting PCR products were mixed with each other and further amplified using E-H primers. The resulting PCR product was digested with the restriction enzymes NcoI and SacII, and inserted into pRA vector to produce an expression vector (pRA-h5Lh5H (LHG0)) for a VL-VH type humanized 528scFv without a linker.

A c-myc peptide tag and His-tag (Hisx6: histidine hexamer tag) had been introduced tandem into its C-terminal of the above vectors for detection and purification, respectively. The base sequence and amino acid sequence of the single-chain antibody (scFv) comprising the heavy chain humanized variable region (5H) of the wild type antibody 528 are shown as SEQ ID NOs 9 and 10.

A:NcoI-5H:
[SEQ ID NO: 11]
5'-NNNCCATGGCCCAGGTGCAACTGGTTCA-3'

B:5H-5L-inverse:
[SEQ ID NO: 12]
5'-GGGCTCTGGGTCATCACGATATCCGAGCTCACGGTAACCAGCG-3'

C:5H-5L:
[SEQ ID NO: 13]
5'-GATATCGTGATGACCCAGAGCCC-3'

D:5L-SacII:
[SEQ ID NO: 14]
5'-NNNCCGCGGCGCGTTTAATTTCCACTTT-3'

E:NcoI-5L:
[SEQ ID NO: 15]
5'-NNNCCATGGATATTGTGATGACCCAGAG-3'

F:5L-5H-inverse:
[SEQ ID NO: 16]
5'-CGCTCTGAACCAGTTGCACCTGTTTAATTTCCACTTTGGTGCCCTGG
CC-3'

G:5L-5H:
[SEQ ID NO: 17]
5'-CAGGTGCAACTGGTTCAGAGCG-3'

H:5H-SacII:
[SEQ ID NO: 18]
5'-NNNCCGCGGAGCTCACGGTAACCAGCGT-3'

EXAMPLE 5

Cell-Growth Inhibition Test with Various Kinds of Antibody Molecules (1)

Each antibody molecule produced in Examples 2 and 3 were studies in MTS assay with respect to their inhibiting activity against human epidermoid cancer cell, 431 (ATCC No. CRL-1555) and human biliary cancer cell, TFK-1 (Cell Resource Center for Biomedical Research, Institute of Development, Aging and Cancer, TOHOKU University, ID:TKG036).

Each cell sample was adjusted by cell counting to contain $5 \times 10^3$ cells per 1004 of RPMI 1640 (10% FBS), and its aliquot of 100 μL was dispensed into each well of a 96-well plate to stand still overnight at 37° C. After being diluted with RPMI to a desired concentration of the antibody according to the present invention, 504 of which was put into each well of the above plate. T-LAK cell or peripheral blood monocyte (PBMC) was diluted with RPMI to a desired E/T (Effector (T-LAK cell or PBRC)/Target cancer cell) ratio, and 50 μL of the cell solution was put into each well of the above plate as well. After being cultured for 48 hours at 37° C., the culture medium was removed. The cells were then washed with PBS, mixed with MTS, PMS and RPMI, and incubated for 30-60 min. at 37° C., followed by the detection of absorbance at 490 nm with a plate reader.

Figure 2:
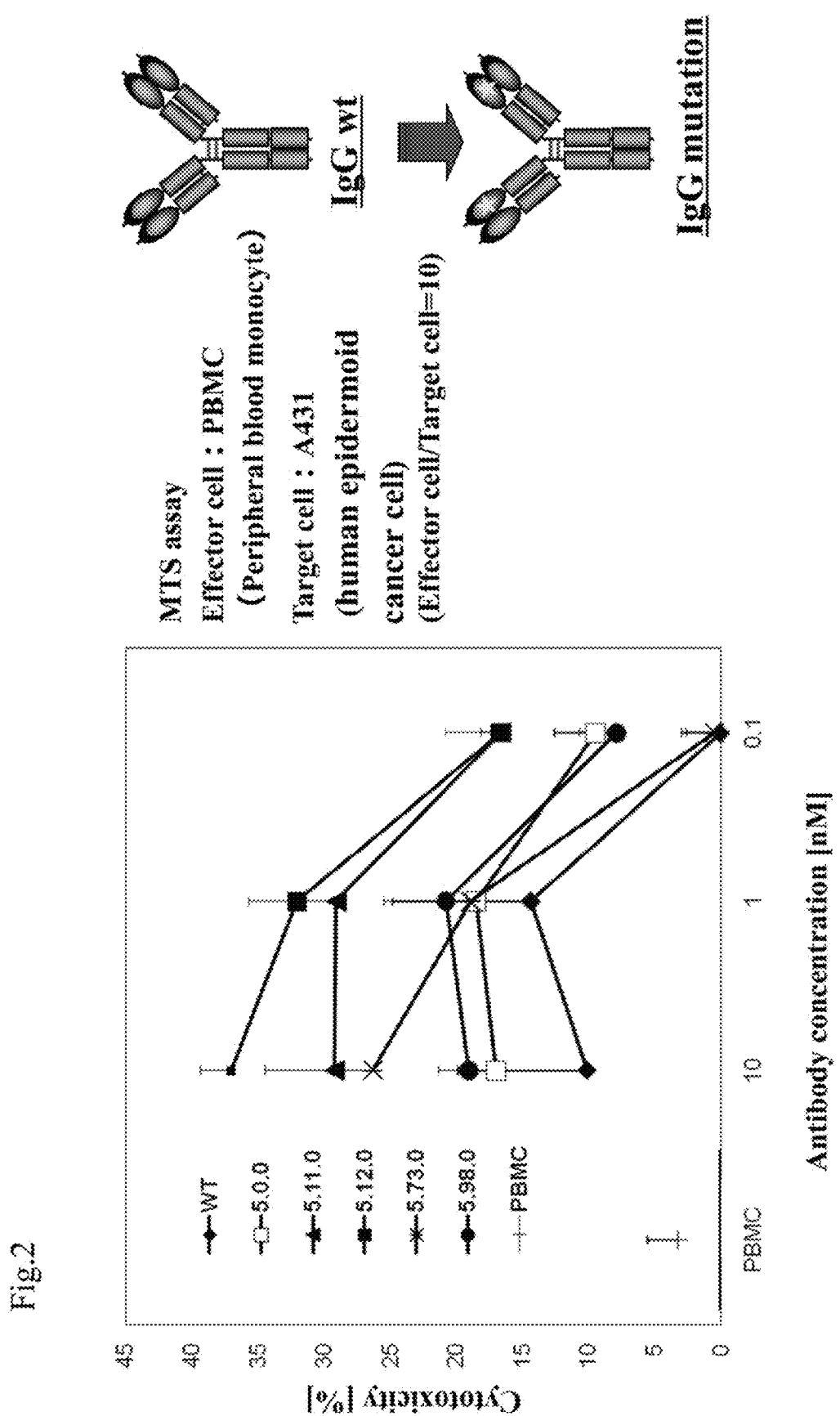
FIG. 2 shows the results of Cytotoxicity Test (cell-growth inhibition test) with the IgG antibody (IgG mutant) comprising as its constituent the mutant of a heavy chain humanized variable region (5H) of the antibody 528.

As shown in FIG. 2, it was confirmed that the IgG antibody (IgG mutant) comprising as its constituent the mutant of the heavy chain humanized variable region (5H) of the antibody 528 showed an increased anti-tumor effects (cytotoxicity) when compared to that of the IgG antibody (IgG wt) without the above mutant.

As shown in FIG. 3, it was confirmed that the diabody-type bispecific antibody (Ex3 mutant) comprising as its constituent the mutant of the heavy chain humanized variable region (5H) of the antibody 528 showed an increased anti-tumor effects (cytotoxicity) when compared to that of the diabody-type bispecific antibody (Ex3) without the above mutant.

As shown in FIG. 4, it was confirmed that the highly functional bispecific antibody (Ex3-scDb-Fc mutant) comprising as its constituent the mutant of the heavy chain humanized variable region (5H) of the antibody 528 showed an increased anti-tumor effects (cytotoxicity) when compared to that of the highly functional bispecific antibody (Ex3-scDb-Fc) without the above mutant.

Figure 5:
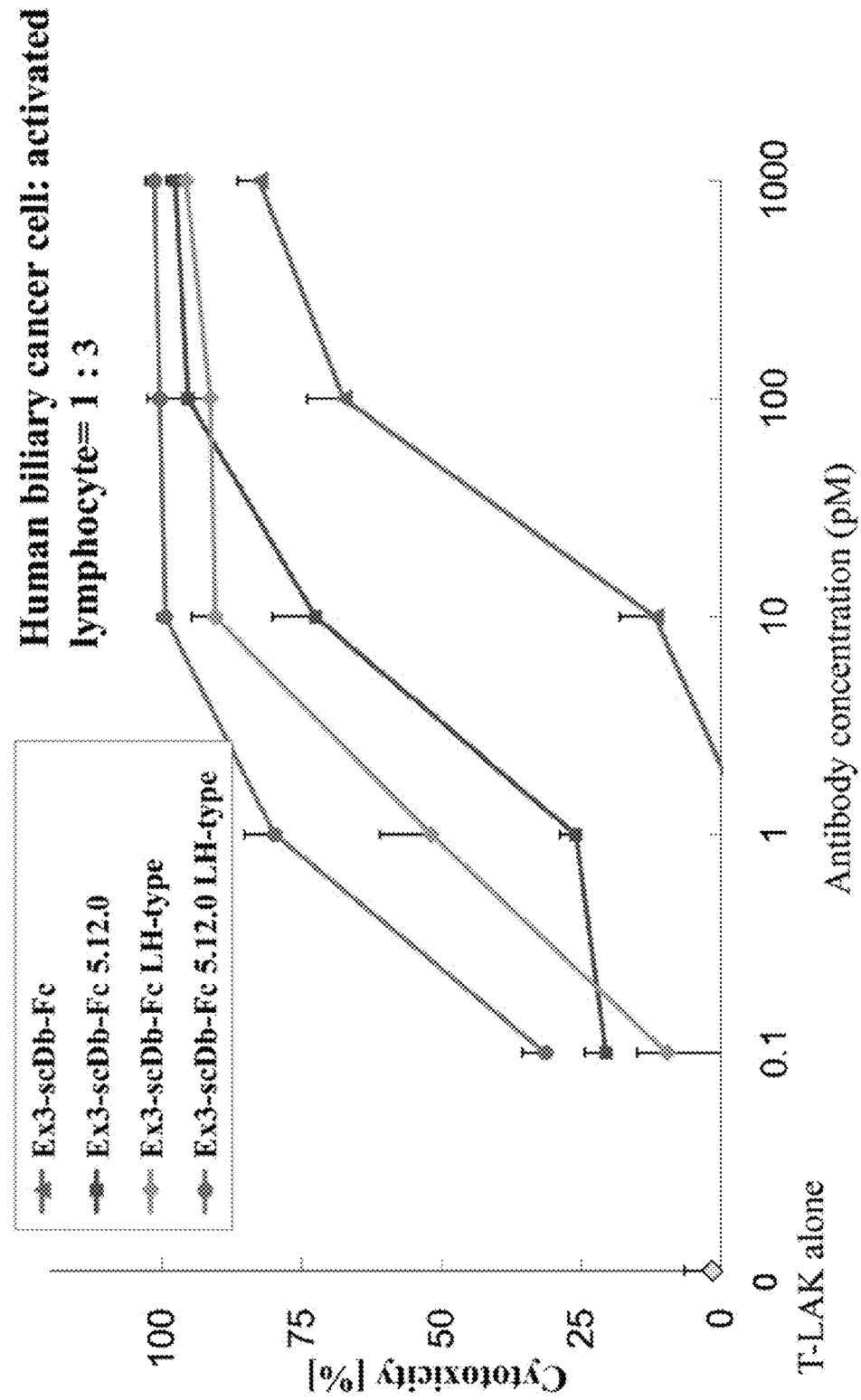
FIG. 5 shows the results of Cytotoxicity Test (cell-growth inhibition test) with the LH-type highly functional bispecific antibody (LH-type Ex3-scDb-Fc mutant) comprising as its constituent the mutant of a heavy chain humanized variable region (5H) of the antibody 528.
Figure 6:
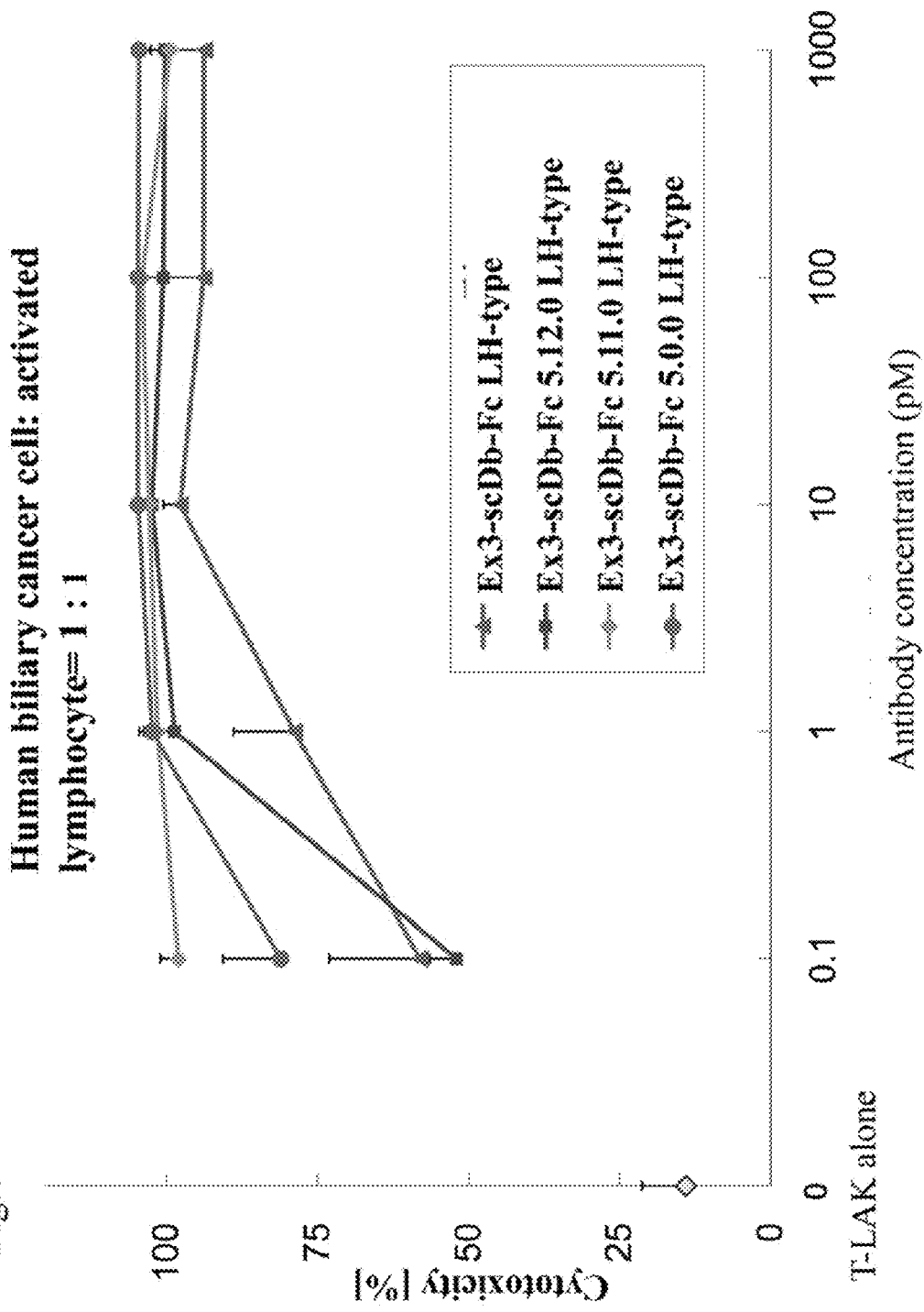
FIG. 6 shows the results of Cytotoxicity Test (cell-growth inhibition test) with the LH-type highly functional bispecific antibody (LH-type Ex3-scDb-Fc mutant) comprising as its constituent the mutant of a heavy chain humanized variable region (5H) of the antibody 528.

As shown in FIG. 5, it was confirmed that the LH-type highly functional bispecific antibody (LH-type Ex3-scDb-Fc mutant) comprising as its constituent the mutant of the heavy chain humanized variable region (5H) of the antibody 528 showed an increased anti-tumor effects (cytotoxicity) when compared to that of the LH-type highly functional bispecific antibody (LH-type Ex3-scDb-Fc) without the above mutant.

EXAMPLE 6

Cell-Growth Inhibition Test with Various Kinds of Antibody Molecules (2)

Each antibody molecule produced in Example 4 were studies in MTS assay with respect to their inhibiting activity against 431 (ATCC No. CRL-1555).

Each cell sample was adjusted by cell counting to contain $2 \times 10^3$ cells per 100 μL of RPMI 1640 (0.5% FBS), and its aliquot of 100 μL was dispensed into each well of a 96-well plate to stand still overnight at 37° C. After being diluted with RPMI to a desired concentration of the antibody according to the present invention, 200 μL of which was put into each well of the above plate, and cultured for 96 hours at 37° C. After the culture medium was removed, the cells were washed with PBS, mixed with MTS, PMS and RPMI, and incubated for 30-60 min. at 37° C., followed by the detection of absorbance at 490 nm with a plate reader.

NOTE: MTS (CellTiter 96 AQueous Non-Radioactive Cell Proliferation Assay, Promega Co.); and
PMS (CellTiter 96 AQueous Non-Radioactive Cell Proliferation Assay, Promega Co.).

Figure 7:
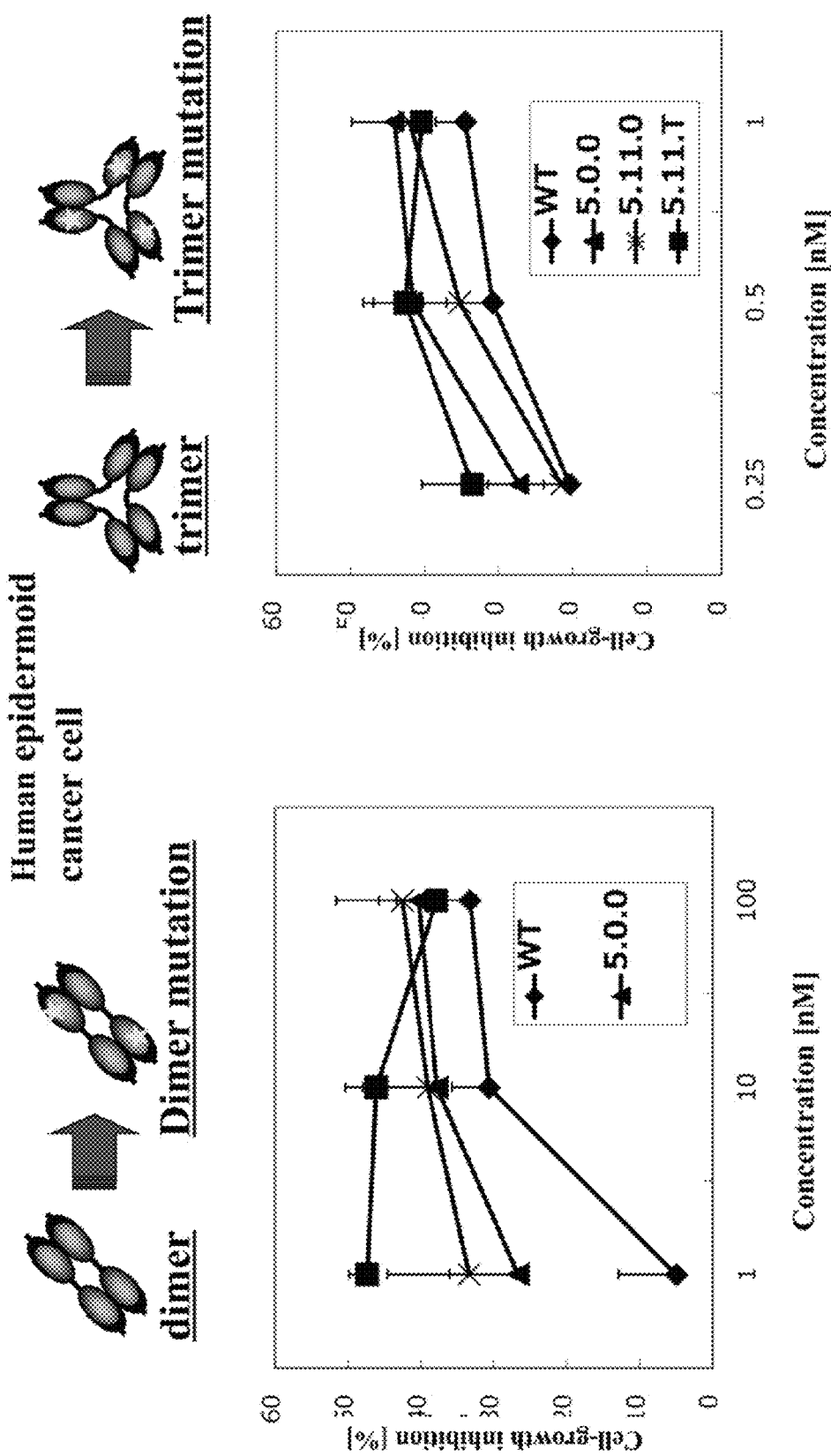
FIG. 7 shows the results of Cytotoxicity Test (cell-growth inhibition test) with the polymerized low-molecular antibody (dimer or trimer mutant) comprising as its constituent the mutant of a heavy chain humanized variable region (5H) of the antibody 528.

As shown in FIG. 7, it was confirmed that the polymerized low-molecular antibody (dimer or trimer mutant) comprising as its constituent the mutant of the heavy chain humanized variable region (5H) of the antibody 528 showed an increased anti-tumor effects (cytotoxicity) when compared to that of the polymerized low-molecular antibody (dimer or trimer) without the mutant.

EXAMPLE 7

A Light Chain Humanized Variable Re on (5L) of an Anti-Human EGFreceptor 1 (Her1) Antibody 528

Based on the crystal structure of the humanized antibody 528 thus obtained, mutations were introduced randomly within and in the vicinity of the CDR of the light chain humanized variable region (5L) of the anti-human EGF receptor 1 antibody 528 by means of a known Site-Specific Mutagenesis (Site-Directed Mutagenesis) while taking solvent-contacting residues into account.

Figure 8:
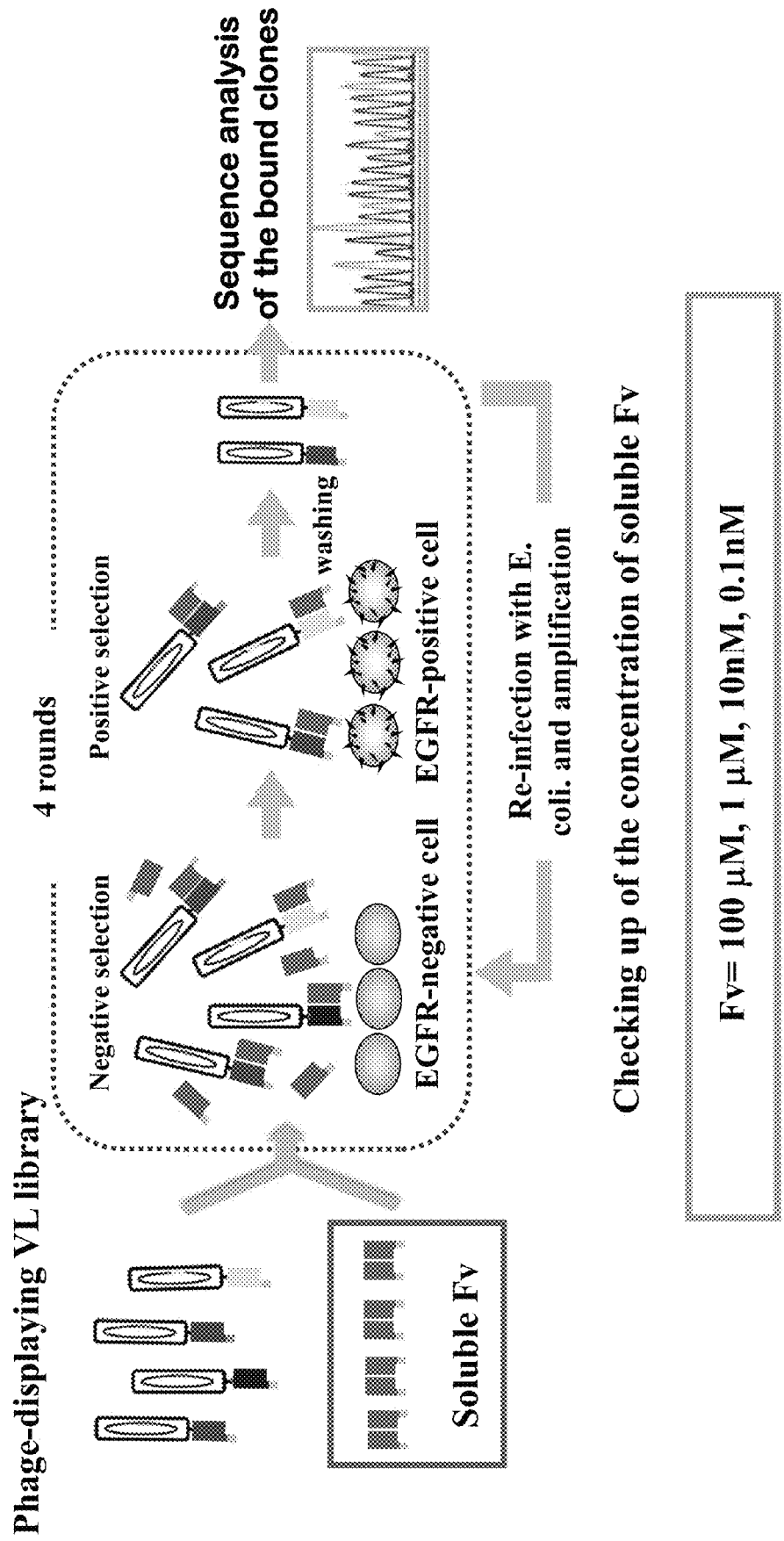
FIG. 8 shows an outline of a method for the selection of the mutant of the light chain humanized variable region (5L) of the antibody 528 by means of phage display that utilizes exchange reaction between VL in a soluble Fv and VL displayed by the phage.

As it was difficult to prepare a soluble VH alone for the conventional phage-display method, a soluble Fv was prepared instead. Positive- and negative-selection were carried out by means of domain-exchange reaction between the VL in the soluble Fv and phage-displaying VL using EGFR-positive CHO cells and EGFR-negative CHO cells, respectively (FIG. 8). The specific amino acid mutations in the resulting mutant VL (designated as "LRS" and "LRL"), and the results of their binding evaluation by means of flow cytometry are shown (FIG. 9).

An Fv co-expression vector of each mutant VL and the heavy chain humanized variable region (VH) of the 528 antibody was constructed. Like in Example 1, it was crudely purified from the culture supernatant of transformed E. coli BL21 strain by means of metal chelate affinity chromatography, subjected to gel filtration chromatography, and then to cation-exchange chromatography for a final purification. The yield of the purified Fv antibody was about 1-10 mg per 1 L of culture medium.

The target antigen, soluble EGFR, was prepared by another CHO cell expression system and purification with metal chelate affinity chromatography. Using the resulting soluble EGFR, kinetic analysis of the mutant Fv was carried out by means of known surface Plasmon resonance technique. An apparatus used in this technique for the determination of surface Plasmon resonance (SPR), BIAcore2000, is composed of three technical elements: sensor chip, micro channel and detection system. Interaction of molecules was reproduced on the sensor chip by means of SPR in the detection system of the apparatus, so that real-time detection could be realized without using any label so as to calculate a binding kinetic (rate) constant and a dissociation kinetic constant. EGFR was fixed on the sensor chip as a ligand by means of amine coupling method, and the detection was made using the mutant Fv as analyte at 25° C. The determination data was analyzed with BIA evaluation soft ware, and kinetic parameters were then calculated based on 1:1 Langmuir binding model.

Figure 10:
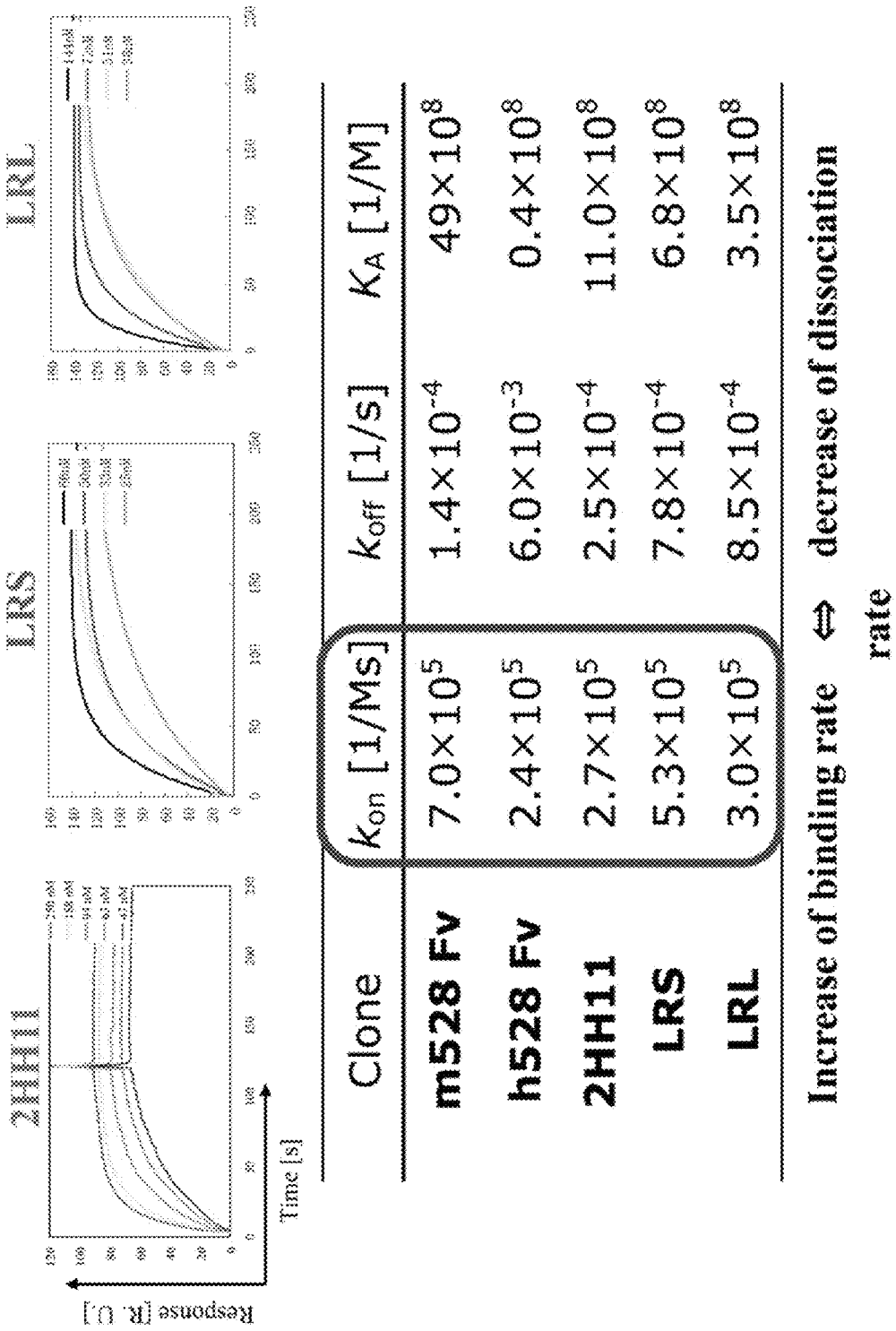
FIG. 10 shows the results of kinetic analysis of the light chain humanized variable region (5L) of the antibody 528 by means of Surface Plasmon resonance technique.

Comparative examples were performed using mouse 528Fv (m528Fv), wild type humanized Fv (h528Fv) and 2HH11 (h528Fv comprising 511 mutant 5.11.0) as a sample. As shown in FIG. 10, the results obtained confirmed that these mutant VLs and the humanized variable region (VH) showed an increased binding kinetic (rate) constant and a decreased dissociation kinetic constant when compared to the wild-type human Fv (h528Fv).

Next, thermodynamic analysis was by means of Isothermal Titration calorimeter (ITC) like in Example 1. The target antigen, soluble EGFR, was prepared by another CHO cell expression system and purification with metal chelate affinity chromatography. The thus purified EGFR at a concentration of 5 μM was added to a titration cell, and the mutant Fv at a concentration of 50 μM was then dropped with time. Binding enthalpy (ΔH) and binding coefficient (Ka) were calculated from the change of calorie during the above titration. Free Energy Change (ΔG) and Binding Entropy Change (ΔS) were then calculated from the above values. The results are shown in FIG. 11. It was confirmed by these results that the binding coefficient (Ka) of the Fv antibodies comprising the above mutants has been increased up to 50-200 times larger than that of an Fv antibody (h528Fv WT) comprising the light chain humanized variable region (5L) of the wild type 528 antibody.

INDUSTRIAL APPLICABILITY

A high cost of the production of an antibody drug has recently become a serious problem. As a result, it has been a worldwide trend to produce a low molecular-weight antibody that can be produced economically in E. coli. On the other hand, although more than ten years have already passed since the low molecular-weight antibody was developed for cancer therapy, it has hardly progressed into a clinical test due to problems in its production and actual therapeutic effects. However, it seems that the antibody drug has the potential as a drug if its production cost or function is improved.

It is expected that the antibody molecule comprising as its constituent the mutant of the heavy chain humanized variable region (5H) or of the light chain humanized variable region (5L) antibody 528 wherein amino acid mutation has been introduced will increase the clinical application of antibody drug, and accelerate the development and seed-search of such molecules by pharmaceutical companies.

What is claimed is:

1. A mutant of a heavy chain humanized variable region (5H) of an anti-human epithelial cell growth factor receptor 1 (Her 1) antibody 528 that consists of the amino acid sequence SEQ ID NO:4, wherein the mutant differs from the amino acid sequence SEQ ID NO: 4 by the replacement of one or more of residues 52, 55, 63, 65, or 66 within its CDR2 with another amino acid, wherein TYR 52 of SEQ ID NO: 4 is replaced by Trp, and wherein, when the mutant is paired with the light chain variable region SEQ ID NO: 2 to form an antibody, the antibody binds human epithelial growth factor receptor 1.

2. A mutant according to claim 1, wherein Ser 55 of SEQ ID NO: 4 is replaced by an amino acid selected from the group consisting of Thr, Lys, Arg, Asn and Gln.

3. A mutant according to claim 1, wherein Lys 63 is replaced by Gln.

4. A mutant according to claim 1, wherein Lys 65 is replaced by Gln.

5. A mutant according to claim 1, wherein Asn 66 is replaced by Gln, Lys or Ser.

6. A mutant according to claim 1, wherein Ala 97 of SEQ ID NO: 4 is further replaced with another amino acid.

7. A mutant according to claim 6, wherein Ala 97 is replaced by Thr.

8. An antibody molecule comprising as its constituent the mutant according to claim 1 and a light chain humanized variable region (5L) of an anti-human epithelial cell growth factor receptor 1 (Her 1) antibody 528 that consists of the amino acid sequence SEQ ID NO: 2, or the amino acid sequence SEQ ID NO: 2 wherein in SEQ ID NO: 2 Lys 55 is replace by Leu, ASP 58 is replaced by Arg, and/or Phe 60 is replaced by Ser or Leu, and wherein said antibody binds human epithelial growth factor receptor 1.

9. The antibody molecule according to claim 8, which is selected from the group consisting of IgG-type antibody molecule, humanized diabody-type bispecific antibody, bispecific antibody, antibody molecule, and polymerized low-molecular antibody.

10. An antibody molecule according to claim 8, further comprising a light chain humanized variable region (OL) and a heavy chain humanized variable region (OH) of an anti-CD3 antibody OKT3 that consist of the amino acid sequences SEQ ID NO:6 and SEQ ID NO:8, respectively.

11. A single-chain polypeptide constituting the antibody molecule of claim 8.

12. A nucleic acid molecule encoding the mutant claim 1, or a single-chain polypeptide constituting an antibody molecule thereof.

13. A nucleic acid molecule encoding two single chain polypeptides constituting the antibody molecule of claim 8.

14. A replicable cloning vector or an expression vector containing the nucleic acid molecule of claim 12.

15. The vector of claim 14, which is a co-expression vector.

16. The vector of claim 14, which is a plasmid vector.

17. A host cell transformed with the vector of claim 14.

18. A method for the production of the antibody molecule of claim 8, comprising culturing a host cell to express two single-chain polypeptides constituting said antibody molecule, collecting and purifying said single-chain polypeptides, assembling the two single-chain polypeptides, and separating and collecting the antibody molecule thus formed.

19. The method of claim 18 wherein the host cell is *E. coli*, and the two single-chain polypeptides are collected from supernatant of a culture medium, periplasm fraction, intracellular soluble fraction or intracellular insoluble fraction.

20. A method for the production of an antibody molecule comprising the mutant of a heavy chain humanized variable region (5H) of claim 1, comprising culturing a host cell transformed with a co-expression vector to express the two single-chain polypeptides constituting said antibody molecule, allowing the transformed cell to form a diabody-type bispecific antibody in said cell, and separating and collecting the bispecific antibody thus formed.

21. A pharmaceutical composition comprising the antibody molecule of claim 8 as an active ingredient.

22. The pharmaceutical composition of claim 21 for use in eliminating, hurting, damaging and/or reducing tumor cells.

* * * * *

SEQUENCE LISTING

```
<160> NUMBER OF SEQ ID NOS: 25

<210> SEQ ID NO 1
<211> LENGTH: 339
<212> TYPE: DNA
<213> ORGANISM: Artificial Sequence
<220> FEATURE:
<223> OTHER INFORMATION: Chimeric Sequence (h5L)
<220> FEATURE:
<221> NAME/KEY: CDS
<222> LOCATION: (1)..(339)

<400> SEQUENCE: 1 gat att gtg atg acc cag agc ccg ctg agc ctg ccg gtg acc cca ggc      48
Asp Ile Val Met Thr Gln Ser Pro Leu Ser Leu Pro Val Thr Pro Gly
1               5                   10                  15 gaa ccg gcg tcg att agc tgc cgc agc tcg cag aac atc gtg cat aat      96
Glu Pro Ala Ser Ile Ser Cys Arg Ser Ser Gln Asn Ile Val His Asn
            20                  25                  30 aac ggc att acc tat ctg gaa tgg tat ctg cag aaa ccg ggc caa agc     144
Asn Gly Ile Thr Tyr Leu Glu Trp Tyr Leu Gln Lys Pro Gly Gln Ser
        35                  40                  45 ccg cag ctg tta att tat aaa gtg agc gat cgc ttt agc ggc gtg ccg     192
Pro Gln Leu Leu Ile Tyr Lys Val Ser Asp Arg Phe Ser Gly Val Pro
```

```
                     50                  55                  60
gat cgc ttt tcg ggc agc ggt agt ggc acc gat ttt acg ctg aaa att     240
Asp Arg Phe Ser Gly Ser Gly Ser Gly Thr Asp Phe Thr Leu Lys Ile
 65                  70                  75                  80 agc cgc gtg gaa gcg gag gat gtt ggc gtg tat tac tgc ttt cag ggc     288
Ser Arg Val Glu Ala Glu Asp Val Gly Val Tyr Tyr Cys Phe Gln Gly
                 85                  90                  95 agc cat atc ccg cca acc ttt ggc caa ggc acc aaa gtg gaa att aaa     336
Ser His Ile Pro Pro Thr Phe Gly Gln Gly Thr Lys Val Glu Ile Lys
                100                 105                 110 cgc                                                                 339
Arg

<210> SEQ ID NO 2
<211> LENGTH: 113
<212> TYPE: PRT
<213> ORGANISM: Artificial Sequence
<220> FEATURE:
<223> OTHER INFORMATION: Synthetic Construct

<400> SEQUENCE: 2

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Asn Ile Val His Asn
                 20                  25                  30

Asn Gly Ile Thr Tyr Leu Glu Trp Tyr Leu Gln Lys Pro Gly Gln Ser
             35                  40                  45

Pro Gln Leu Leu Ile Tyr Lys Val Ser Asp Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ile Pro Pro Thr Phe Gly Gln Gly Thr Lys Val Glu Ile Lys
                100                 105                 110

Arg

<210> SEQ ID NO 3
<211> LENGTH: 354
<212> TYPE: DNA
<213> ORGANISM: Artificial Sequence
<220> FEATURE:
<223> OTHER INFORMATION: Chimeric Sequence (h5H)
<220> FEATURE:
<221> NAME/KEY: CDS
<222> LOCATION: (1)..(354)

<400> SEQUENCE: 3 cag gtg caa ctg gtt cag agc ggc gcg gaa gtg aaa aag ccg ggc gcg     48
Gln Val Gln Leu Val Gln Ser Gly Ala Glu Val Lys Lys Pro Gly Ala
 1               5                  10                  15 tcg gtt aaa gtg agc tgc aaa gcc tca ggc tat acc ttt acg agc tac     96
Ser Val Lys Val Ser Cys Lys Ala Ser Gly Tyr Thr Phe Thr Ser Tyr
                 20                  25                  30 tgg atg cat tgg gtg cgc cag gcc ccg ggt cag ggc ctg gaa tgg atg    144
Trp Met His Trp Val Arg Gln Ala Pro Gly Gln Gly Leu Glu Trp Met
             35                  40                  45 ggt aac att tat ccg ggc agc ggt ggc acc aac tat gcg gaa aaa ttt    192
Gly Asn Ile Tyr Pro Gly Ser Gly Gly Thr Asn Tyr Ala Glu Lys Phe
         50                  55                  60
```

```
aag aac cgc gtg acc atg acg cgt gat acc agc att tcg acg gcc tat    240
Lys Asn Arg Val Thr Met Thr Arg Asp Thr Ser Ile Ser Thr Ala Tyr
 65                  70                  75                  80 atg gaa ctg agc cgc ctg cgt agc gat gac acc gcc gtg tat tac tgc    288
Met Glu Leu Ser Arg Leu Arg Ser Asp Asp Thr Ala Val Tyr Tyr Cys
             85                  90                  95 gcg cgc agt ggc ggt ccg tat ttt ttc gat tac tgg ggc cag ggt acg    336
Ala Arg Ser Gly Gly Pro Tyr Phe Phe Asp Tyr Trp Gly Gln Gly Thr
100                 105                 110 ctg gtt acc gtg agc tcg                                            354
Leu Val Thr Val Ser Ser
        115
```

```
<210> SEQ ID NO 4
<211> LENGTH: 118
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Tyr Pro Gly Ser Gly Gly Thr Asn Tyr Ala Glu Lys Phe
    50                  55                  60

Lys Asn Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Gly Gly Pro Tyr Phe Phe Asp Tyr Trp Gly Gln Gly Thr
        100                 105                 110

Leu Val Thr Val Ser Ser
        115
```

```
<210> SEQ ID NO 5
<211> LENGTH: 321
<212> TYPE: DNA
<213> ORGANISM: Artificial Sequence
<220> FEATURE:
<223> OTHER INFORMATION: Chimeric Sequence (hOL)
<220> FEATURE:
<221> NAME/KEY: CDS
<222> LOCATION: (1)..(321)

<400> SEQUENCE: 5 gat atc cag atg acc cag agc ccg agc tct ctg agc gcg agc gtg ggc     48
Asp Ile Gln Met Thr Gln Ser Pro Ser Ser Leu Ser Ala Ser Val Gly
1               5                   10                  15 gat cgc gtg acc att acg tgc agc gcg tct agc tct gtg agc tat atg     96
Asp Arg Val Thr Ile Thr Cys Ser Ala Ser Ser Ser Val Ser Tyr Met
            20                  25                  30 aac tgg tac cag caa acc cca ggc aaa gcg ccg aaa cgc tgg att tat    144
Asn Trp Tyr Gln Gln Thr Pro Gly Lys Ala Pro Lys Arg Trp Ile Tyr
        35                  40                  45 gat acc agc aaa ctg gcg agc ggc gtg ccg agc cgc ttt agc ggc tct    192
Asp Thr Ser Lys Leu Ala Ser Gly Val Pro Ser Arg Phe Ser Gly Ser
    50                  55                  60
```

```
ggt agc ggc acc gat tat acg ttt acc att agc tct ctg cag ccg gaa        240
Gly Ser Gly Thr Asp Tyr Thr Phe Thr Ile Ser Ser Leu Gln Pro Glu
 65                  70                  75                  80 gat att gcg acc tat tac tgc cag caa tgg agc tct aac ccg ttt acc        288
Asp Ile Ala Thr Tyr Tyr Cys Gln Gln Trp Ser Ser Asn Pro Phe Thr
                 85                  90                  95 ttt ggc cag ggt acc aaa ctg cag att acc cgc                            321
Phe Gly Gln Gly Thr Lys Leu Gln Ile Thr Arg
            100                 105
```

```
<210> SEQ ID NO 6
<211> LENGTH: 107
<212> TYPE: PRT
<213> ORGANISM: Artificial Sequence
<220> FEATURE:
<223> OTHER INFORMATION: Synthetic Construct

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Val Ser Tyr Met
             20                  25                  30

Asn Trp Tyr Gln Gln Thr Pro Gly Lys Ala Pro Lys Arg Trp Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
            100                 105
```

```
<210> SEQ ID NO 7
<211> LENGTH: 357
<212> TYPE: DNA
<213> ORGANISM: Artificial Sequence
<220> FEATURE:
<223> OTHER INFORMATION: Chimeric Sequence (hOH)
<220> FEATURE:
<221> NAME/KEY: CDS
<222> LOCATION: (1)..(357)

<400> SEQUENCE: 7 cag gtg caa ctg gtg cag agc ggc ggt ggc gtt gtg cag ccg ggc cgc        48
Gln Val Gln Leu Val Gln Ser Gly Gly Gly Val Val Gln Pro Gly Arg
 1               5                  10                  15 agc ctg cgc ctg tct tgc aaa gcg agc ggc tat acc ttt acg cgc tat        96
Ser Leu Arg Leu Ser Cys Lys Ala Ser Gly Tyr Thr Phe Thr Arg Tyr
             20                  25                  30 acc atg cat tgg gtg cgc cag gcg ccg ggc aaa ggt ctg gaa tgg att       144
Thr Met His Trp Val Arg Gln Ala Pro Gly Lys Gly Leu Glu Trp Ile
             35                  40                  45 ggc tat att aac ccg tct cgc ggc tat acc aac tat aat cag aaa gtg       192
Gly Tyr Ile Asn Pro Ser Arg Gly Tyr Thr Asn Tyr Asn Gln Lys Val
         50                  55                  60 aaa gat cgc ttt acc att agc cgc gat aac tct aaa aac acc gcg ttt       240
Lys Asp Arg Phe Thr Ile Ser Arg Asp Asn Ser Lys Asn Thr Ala Phe
 65                  70                  75                  80 ctg cag atg gat agc ctg cgc ccg gaa gat acc ggc gtg tat ttt tgc       288
Leu Gln Met Asp Ser Leu Arg Pro Glu Asp Thr Gly Val Tyr Phe Cys
                 85                  90                  95
```

```
gcg cgc tac tat gat gac cat tat agc ctg gat tat tgg ggc cag ggc      336
Ala Arg Tyr Tyr Asp Asp His Tyr Ser Leu Asp Tyr Trp Gly Gln Gly
            100                 105                 110 acc ccg gtg acc gtt agc tcg                                          357
Thr Pro Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115

<210> SEQ ID NO 9
<211> LENGTH: 798
<212> TYPE: DNA
<213> ORGANISM: Artificial Sequence
<220> FEATURE:
<223> OTHER INFORMATION: 528scFv
<220> FEATURE:
<221> NAME/KEY: CDS
<222> LOCATION: (1)..(798)

<400> SEQUENCE: 9 cag gtg caa ctg gtt cag agc ggc gcg gaa gtg aaa aag ccg ggc gcg      48
Gln Val Gln Leu Val Gln Ser Gly Ala Glu Val Lys Lys Pro Gly Ala
1               5                   10                  15 tcg gtt aaa gtg agc tgc aaa gcc tca ggc tat acc ttt acg agc tac      96
Ser Val Lys Val Ser Cys Lys Ala Ser Gly Tyr Thr Phe Thr Ser Tyr
            20                  25                  30 tgg atg cat tgg gtg cgc cag gcc ccg ggt cag ggc ctg gaa tgg atg      144
Trp Met His Trp Val Arg Gln Ala Pro Gly Gln Gly Leu Glu Trp Met
        35                  40                  45 ggt aac att tat ccg ggc agc ggt ggc acc aac tat gcg gaa aaa ttt      192
Gly Asn Ile Tyr Pro Gly Ser Gly Gly Thr Asn Tyr Ala Glu Lys Phe
    50                  55                  60 aag aac cgc gtg acc atg acg cgt gat acc agc att tcg acg gcc tat      240
Lys Asn Arg Val Thr Met Thr Arg Asp Thr Ser Ile Ser Thr Ala Tyr
65                  70                  75                  80 atg gaa ctg agc cgc ctg cgt agc gat gac acc gcc gtg tat tac tgc      288
Met Glu Leu Ser Arg Leu Arg Ser Asp Asp Thr Ala Val Tyr Tyr Cys
                85                  90                  95
```

```
gcg cgc agt ggc ggt ccg tat ttt ttc gat tac tgg ggc cag ggt acg      336
Ala Arg Ser Gly Gly Pro Tyr Phe Phe Asp Tyr Trp Gly Gln Gly Thr
            100                 105                 110 ctg gtt acc gtg agc tcg gcc ggg ggc ggt tcg gat atc gtg atg          384
Leu Val Thr Val Ser Ser Ala Gly Gly Gly Ser Asp Ile Val Met
        115                 120                 125 acc cag agc ccg ctg agc ctg ccg gtg acc cca ggc gaa ccg gcg tcg      432
Thr Gln Ser Pro Leu Ser Leu Pro Val Thr Pro Gly Glu Pro Ala Ser
130                 135                 140 att agc tgc cgc agc tcg cag aac atc gtg cat aat aac ggc att acc      480
Ile Ser Cys Arg Ser Ser Gln Asn Ile Val His Asn Asn Gly Ile Thr
145                 150                 155                 160 tat ctg gaa tgg tat ctg cag aaa ccg ggc caa agc ccg cag ctg tta      528
Tyr Leu Glu Trp Tyr Leu Gln Lys Pro Gly Gln Ser Pro Gln Leu Leu
                165                 170                 175 att tat aaa gtg agc gat cgc ttt agc ggc gtg ccg gat cgc ttt tcg      576
Ile Tyr Lys Val Ser Asp Arg Phe Ser Gly Val Pro Asp Arg Phe Ser
            180                 185                 190 ggc agc ggt agt ggc acc gat ttt acg ctg aaa att agc cgc gtg gaa      624
Gly Ser Gly Ser Gly Thr Asp Phe Thr Leu Lys Ile Ser Arg Val Glu
        195                 200                 205 gcg gag gat gtt ggc gtg tat tac tgc ttt cag ggc agc cat atc ccg      672
Ala Glu Asp Val Gly Val Tyr Tyr Cys Phe Gln Gly Ser His Ile Pro
210                 215                 220 cca acc ttt ggc cag ggc acc aaa gtg gaa att aaa cgc gcc gcg gct      720
Pro Thr Phe Gly Gln Gly Thr Lys Val Glu Ile Lys Arg Ala Ala Ala
225                 230                 235                 240 gca gaa caa aaa ctc atc tca gaa gag gat ctg aat cta ggg ggt ggc      768
Ala Glu Gln Lys Leu Ile Ser Glu Glu Asp Leu Asn Leu Gly Gly Gly
                245                 250                 255 atg cgc ggc tcg cac cat cat cac cac cat                              798
Met Arg Gly Ser His His His His His His
            260                 265
```

<210> SEQ ID NO 10
<211> LENGTH: 266
<212> TYPE: PRT
<213> ORGANISM: Artificial Sequence
<220> FEATURE:
<223> OTHER INFORMATION: Synthetic Construct

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Tyr Pro Gly Ser Gly Thr Asn Tyr Ala Glu Lys Phe
    50                  55                  60

Lys Asn Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser Ala Gly Gly Gly Ser Asp Ile Val Met
        115                 120                 125
```

```
Thr Gln Ser Pro Leu Ser Leu Pro Val Thr Pro Gly Glu Pro Ala Ser
        130                 135                 140
Ile Ser Cys Arg Ser Ser Gln Asn Ile Val His Asn Asn Gly Ile Thr
145                 150                 155                 160
Tyr Leu Glu Trp Tyr Leu Gln Lys Pro Gly Gln Ser Pro Gln Leu Leu
                165                 170                 175
Ile Tyr Lys Val Ser Asp Arg Phe Ser Gly Val Pro Asp Arg Phe Ser
                180                 185                 190
Gly Ser Gly Ser Gly Thr Asp Phe Thr Leu Lys Ile Ser Arg Val Glu
            195                 200                 205
Ala Glu Asp Val Gly Val Tyr Tyr Cys Phe Gln Gly Ser His Ile Pro
    210                 215                 220
Pro Thr Phe Gly Gln Gly Thr Lys Val Glu Ile Lys Arg Ala Ala Ala
225                 230                 235                 240
Ala Glu Gln Lys Leu Ile Ser Glu Glu Asp Leu Asn Leu Gly Gly Gly
                245                 250                 255
Met Arg Gly Ser His His His His His His
            260                 265
```

<210> SEQ ID NO 11
<211> LENGTH: 28
<212> TYPE: DNA
<213> ORGANISM: Artificial Sequence
<220> FEATURE:
<223> OTHER INFORMATION: Primer A:NcoI-5H
<220> FEATURE:
<221> NAME/KEY: misc_feature
<222> LOCATION: (1)..(3)
<223> OTHER INFORMATION: Any

<400> SEQUENCE: 11
nnnccatggc ccaggtgcaa ctggttca                                      28

<210> SEQ ID NO 12
<211> LENGTH: 43
<212> TYPE: DNA
<213> ORGANISM: Artificial Sequence
<220> FEATURE:
<223> OTHER INFORMATION: Primer B:5H-5L

<400> SEQUENCE: 12
gggctctggg tcatcacgat atccgagctc acggtaacca gcg                     43

<210> SEQ ID NO 13
<211> LENGTH: 23
<212> TYPE: DNA
<213> ORGANISM: Artificial Sequence
<220> FEATURE:
<223> OTHER INFORMATION: Primer C:5H-5L

<400> SEQUENCE: 13
gatatcgtga tgacccagag ccc                                           23

<210> SEQ ID NO 14
<211> LENGTH: 28
<212> TYPE: DNA
<213> ORGANISM: Artificial Sequence
<220> FEATURE:
<223> OTHER INFORMATION: Primer D:5L-SacII
<220> FEATURE:
<221> NAME/KEY: misc_feature
<222> LOCATION: (1)..(3)
<223> OTHER INFORMATION: Any

<400> SEQUENCE: 14
nnnccgcggc gcgtttaatt tccacttt                                          28

<210> SEQ ID NO 15
<211> LENGTH: 28
<212> TYPE: DNA
<213> ORGANISM: Artificial Seqeunce
<220> FEATURE:
<223> OTHER INFORMATION: Primer E:NcoI-5L
<220> FEATURE:
<221> NAME/KEY: 1misc_feature
<222> LOCATION: (1)..(3)
<223> OTHER INFORMATION: Any
<220> FEATURE:
<221> NAME/KEY: misc_feature
<222> LOCATION: (1)..(3)
<223> OTHER INFORMATION: Any

<400> SEQUENCE: 15
nnnccatgga tattgtgatg acccagag                                          28

<210> SEQ ID NO 16
<211> LENGTH: 49
<212> TYPE: DNA
<213> ORGANISM: Artificial Sequence
<220> FEATURE:
<223> OTHER INFORMATION: Primer F:5L-5H-inverse

<400> SEQUENCE: 16
cgctctgaac cagttgcacc tgtttaattt ccactttggt gccctggcc                   49

<210> SEQ ID NO 17
<211> LENGTH: 22
<212> TYPE: DNA
<213> ORGANISM: Artificial Sequence
<220> FEATURE:
<223> OTHER INFORMATION: Primer G:5L-5H

<400> SEQUENCE: 17
caggtgcaac tggttcagag cg                                                22

<210> SEQ ID NO 18
<211> LENGTH: 28
<212> TYPE: DNA
<213> ORGANISM: Artificial Sequence
<220> FEATURE:
<223> OTHER INFORMATION: Primer H:5H-SacII
<220> FEATURE:
<221> NAME/KEY: misc_feature
<222> LOCATION: (1)..(3)
<223> OTHER INFORMATION: n is a, c, g, or t

<400> SEQUENCE: 18
nnnccgcgga gctcacggta accagcgt                                          28

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide

<400> SEQUENCE: 19

Asn Ile Tyr Pro Gly Ser Gly Gly Thr Asn Tyr Ala Glu Lys Phe Lys
1               5                   10                  15

Asn

```
<210> SEQ ID NO 20
<211> LENGTH: 17
<212> TYPE: PRT
<213> ORGANISM: Artificial Sequence
<220> FEATURE:
<223> OTHER INFORMATION: Synthetic peptide

<400> SEQUENCE: 20

Asn Ile Trp Pro Gly Ser Gly Gly Thr Asn Tyr Ala Glu Lys Phe Lys
1               5                   10                  15
Asn

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide

<400> SEQUENCE: 21

Asn Ile Trp Pro Gly Thr Gly Gly Thr Asn Tyr Ala Glu Lys Phe Gln
1               5                   10                  15
Gln

<210> SEQ ID NO 22
<211> LENGTH: 17
<212> TYPE: PRT
<213> ORGANISM: Artificial Sequence
<220> FEATURE:
<223> OTHER INFORMATION: Synthetic peptide

<400> SEQUENCE: 22

Asn Ile Trp Pro Gly Lys Gly Gly Thr Asn Tyr Ala Glu Lys Phe Gln
1               5                   10                  15
Lys

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Asn Ile Trp Pro Gly Asn Gly Gly Thr Asn Tyr Ala Glu Gln Phe Lys
1               5                   10                  15
Gln

<210> SEQ ID NO 24
<211> LENGTH: 17
<212> TYPE: PRT
<213> ORGANISM: Artificial Sequence
<220> FEATURE:
<223> OTHER INFORMATION: Synthetic peptide

<400> SEQUENCE: 24

Asn Ile Trp Pro Gly Gln Gly Gly Thr Asn Tyr Ala Glu Lys Phe Lys
1               5                   10                  15
Ser

<210> SEQ ID NO 25
<211> LENGTH: 17
<212> TYPE: PRT
```

```
<213> ORGANISM: Artificial Sequence
<220> FEATURE:
<223> OTHER INFORMATION: Synthetic peptide

<400> SEQUENCE: 25

Asn Ile Trp Pro Gly Thr Gly Gly Thr Asn Tyr Ala Glu Lys Phe Gln
1               5                   10                  15

Gln
```